US011839502B2

(12) United States Patent
Smith

(10) Patent No.: US 11,839,502 B2
(45) Date of Patent: Dec. 12, 2023

(54) PORTABLE HEAD CT SCANNER

(71) Applicant: TEK84 INC., Poway, CA (US)

(72) Inventor: Steven Winn Smith, San Diego, CA (US)

(73) Assignee: TEK84 INC., Poway, CA (US)

( * ) Notice: Subject to any disclaimer, the term of this patent is extended or adjusted under 35 U.S.C. 154(b) by 0 days.

(21) Appl. No.: 18/118,000

(22) Filed: Mar. 6, 2023

(65) Prior Publication Data

US 2023/0320677 A1   Oct. 12, 2023

Related U.S. Application Data

(60) Provisional application No. 63/316,681, filed on Mar. 4, 2022.

(51) Int. Cl.
*A61B 6/00* (2006.01)
*A61B 6/03* (2006.01)
*A61B 6/04* (2006.01)

(52) U.S. Cl.
CPC ............. *A61B 6/032* (2013.01); *A61B 6/04* (2013.01); *A61B 6/4275* (2013.01); *A61B 6/4405* (2013.01); *A61B 6/5229* (2013.01)

(58) Field of Classification Search
CPC ......... A61B 6/032; A61B 6/04; A61B 6/4275; A61B 6/4405
See application file for complete search history.

(56) References Cited

U.S. PATENT DOCUMENTS

| 2005/0135560 A1* | 6/2005 | Dafni ................. A61B 6/56 378/101 |
| 2015/0265225 A1 | 9/2015 | Crawford et al. |
| 2015/0282774 A1 | 10/2015 | Lee et al. |
| 2021/0137478 A1 | 5/2021 | Wang et al. |

FOREIGN PATENT DOCUMENTS

WO    WO 2017/180566 A2    10/2017

OTHER PUBLICATIONS

International Search Repport and Written Opinion dated May 26, 2023 for International Application No. PCT/US2023/014647, filed Mar. 6, 2023.

* cited by examiner

*Primary Examiner* — Dani Fox
(74) *Attorney, Agent, or Firm* — Sheppard, Mullin, Richter & Hampton LLP

(57) ABSTRACT

Imaging systems and methods are provided for scanning a patient's head using a portable CT scanner. An imaging assembly can comprise a portable scan board on which a patient is positioned, and a corresponding portable CT scanner positioned and locked onto the portable scan board. The portable CT scanner and the portable scan board can form a portable CT scanning assembly capable of rotating an X-ray source and corresponding X-ray detector around the patient's head to transmit X-rays through the patient's head at one or more angles, while translating across the portable scan board to scan one or more portions of the patient's head. A composite image reconstructed based on the rotational and translational scanning is generated representing one or more interior aspects of the patient's head.

20 Claims, 16 Drawing Sheets

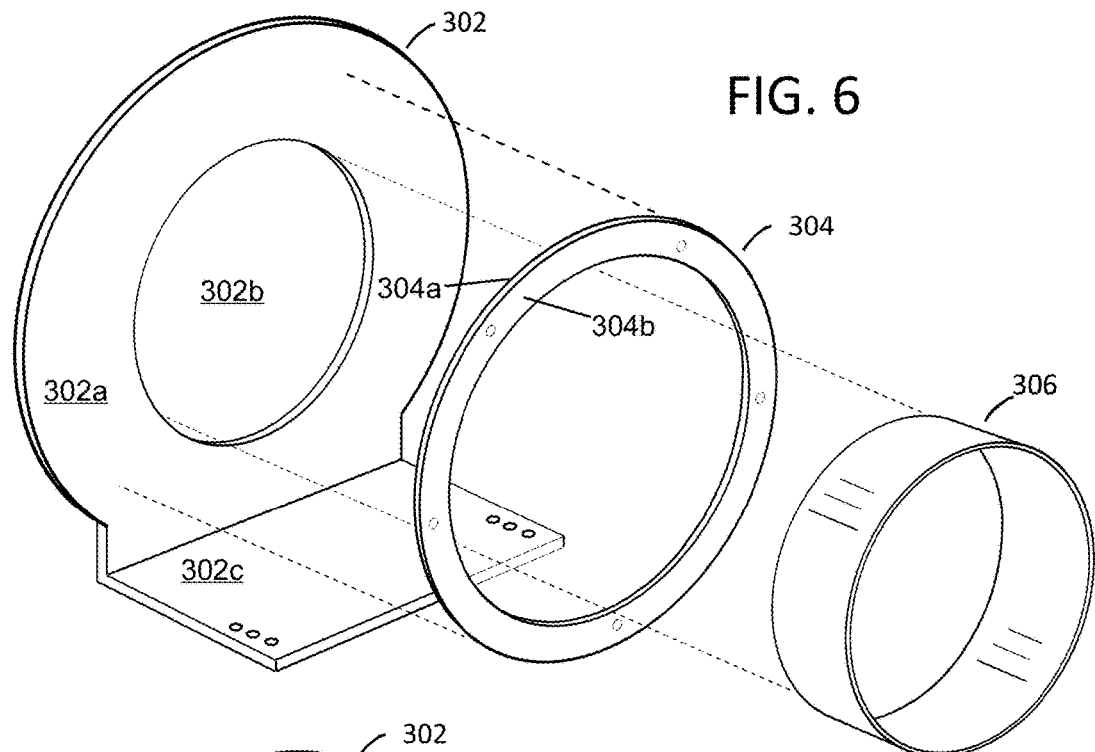
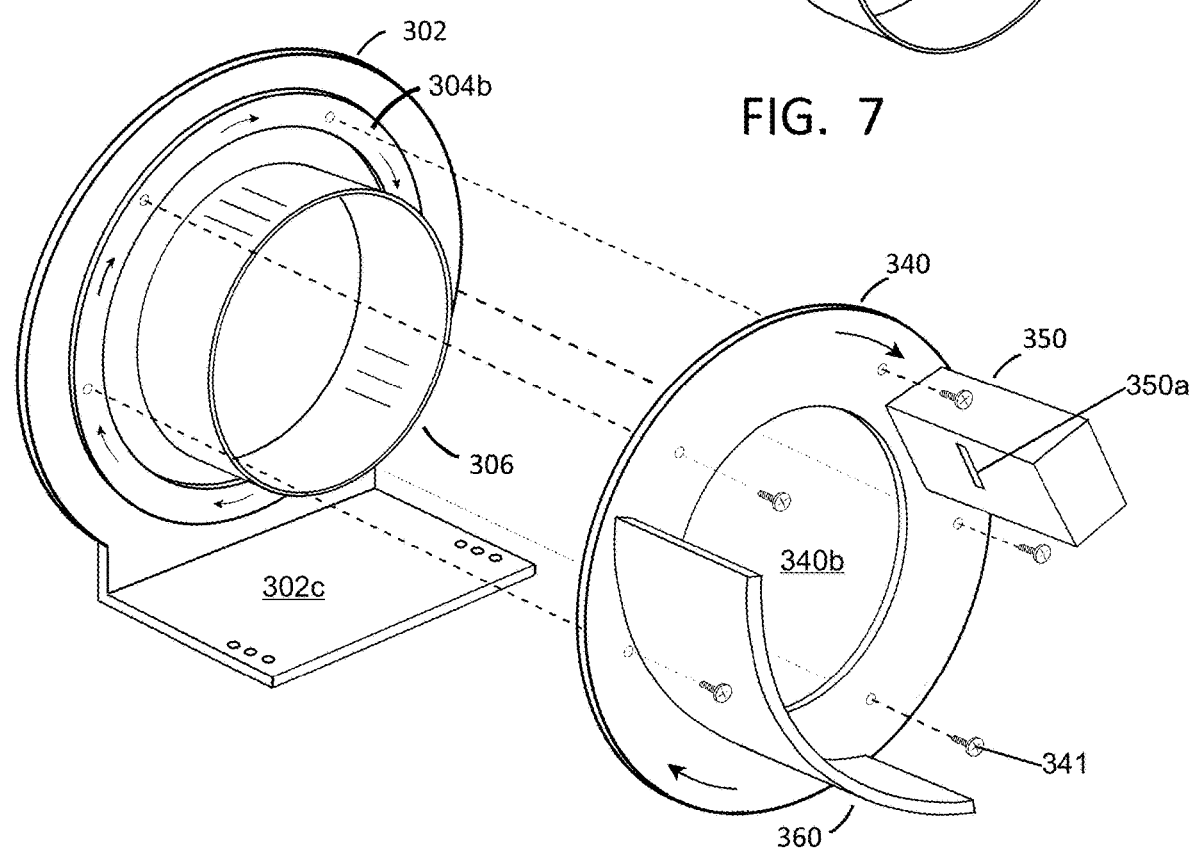

PORTABLE HEAD CT SCANNER

CROSS-REFERENCE TO RELATED APPLICATION

The present application claims priority to U.S. Provisional Patent Application No. 63/316,681, filed Mar. 4, 2022 and titled "ULTRA-PORTABLE CT HEAD SCANNER," which is incorporated herein by reference in its entirety.

TECHNICAL FIELD

The present disclosure is generally related to computed tomography (CT) imaging, and more particularly to a small-scale, portable CT imaging device/system.

BACKGROUND

Computed/computerized tomography (CT) is a diagnostic technique in medicine used to scan and produce images of a body's interior, e.g., bones, muscles, fat, organs, and blood vessels. Devices used for CT scanning rely on X-ray imaging in conjunction with computer processing to generate detailed images of the interior anatomy of a body, such as a human body, animal body, or even non-living objects. More than 100 million medical CT examinations are conducted each year across the world.

BRIEF DESCRIPTION OF THE DRAWINGS

FIG. 6 illustrates an exploded view of a CT scanner base in accordance with some embodiments of the present invention.

FIG. 7 illustrates an exploded view of the base of FIG. 6 with a corresponding X-ray detector and X-ray source.

Figure 1:
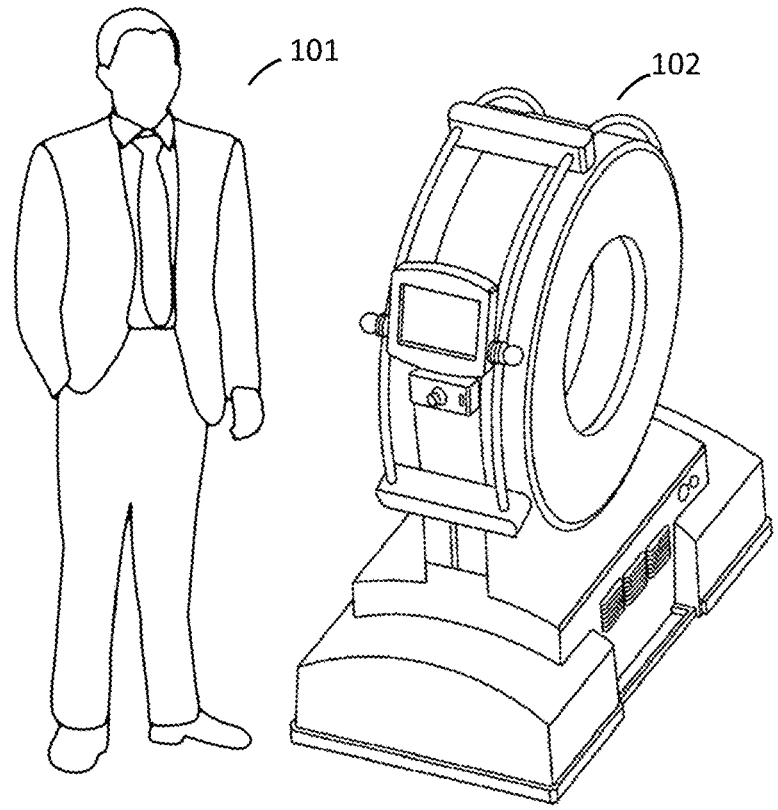
FIG. 1 illustrates a traditional imaging system in comparison with a human figure.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION

Embodiments of the disclosed technology are directed to a portable head CT scanner that is sized to allow for hand-carry transport to/from a subject. As will be described in greater detail below, these portable head CT scanners can be used to scan a section or portion of a subject, e.g., the head or cranial area of a human patient. Use of such portable head CT scanners, unlike traditional CT scanners (described below) involve only minor/minimal repositioning of a patient resting in a bed. The details of some example embodiments of the systems and methods of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description and be within the scope of the present disclosure. For example, it should be understood that although embodiments of the disclosed technology will likely be used in a medical context/setting for scanning the head/cranial region of a patient, the use of embodiments are not necessarily limited to performing head CT scanning. Embodiments can be used for other purposes/in other contexts.

In particular, some embodiments of the disclosed technology may comprise a portable head CT scanner (smaller than traditional fixed-site use and transportable CT scanners), that can be easily moved to and from different areas of operation. For example, a portable head CT scanner configured in accordance with various embodiments may include appropriately-sized component parts that allow the portable head CT scanner to be moved in carrying/storage cases that are compact and light enough to be carried by a single person, unassisted. Furthermore, such a portable head CT scanner can acquire a scan of a patient's brain while tolerating incidental movement of the patient resting in a bed. The patient can be positioned in a supine position on a surface, such as on a hospital bed or other surface. The patient's shoulders can be elevated to position a scan board under the patient. It should be understood that use of the scan board is not limited to situations where a subject is bed-bound, but can be used in other scenarios or situations where a subject is on another surface. The portable head CT scanner can be positioned on the scan board and connected to the scan board to eliminate relative movement between the patient and the portable head CT scanner. The portable head CT scanner can be manipulated on the scan board, and operated to acquire a CT scanned image(s) of the patient's brain.

From the above (and further description below) it can be appreciated that embodiments of the disclosed technology can negate problems associated with both traditional fixed-site use and transportable CT scanners. The embodiments significantly reduce the amount of movement a patient has to endure in order to conduct CT scanning or imaging (e.g., lifting a patient's shoulders to position the patient on a scan board versus transporting a patient to/from a dedicated CT scanning room, and sometimes lifting the entire body of the patient to effectuate traditional CT scanning). Moreover, the portable nature of such portable head CT scanners coincides with the use of components that alleviate/reduce their power needs compared to traditional CT scanners, i.e., smaller size/componentry requires less power to operate. Additionally, and despite the smaller size and portable operation, vibration and motion artifacts are still avoided.

CT scanning is an important, oftentimes critical diagnostic technique typically used in, but not limited to, the medical field. Devices used to perform CT scans, referred to as CT scanners, typically comprise a rotating X-ray source (usually containing an X-ray tube) and a row of X-ray detectors (and perhaps shielding elements) mounted on a rotating gantry. The row of X-ray detectors measure the attenuation of X-ray signals transmitted by the X-ray source through an object/subject (and different tissues/elements therein) situated within the bore of the gantry, before being detected by the row of X-ray detectors. Multiple X-ray measurements can be obtained from different angles, which can then be (computer) processed using tomographic (cross-sectional) reconstruction techniques or algorithms. The result is a series or set of tomographic images, which can be thought of as virtual slices, of the object/subject.

As mentioned above, more than 100 million medical CT examinations are conducted each year across the world. Traditional CT scanners (whether used for full body scanning or just for scanning the head) are designed for fixed-site use and are generally large in size. Here, fixed-site use can refer to a scanner having to be installed in a particular location, and kept at the installation location during operation. Accordingly, facilities such as hospitals, typically dedicate an entire room to a traditional CT scanner. As can be appreciated, this fixed-site use limitation of traditional CT scanners is due in part, to the large size of such traditional CT scanners. It should also be noted that traditional CT scanners require upwards of 60 kilowatts of electrical power to operate, oftentimes requiring a wired connection to mains power.

Returning to the size aspect, for perspective, traditional CT scanners can be approximately 8 feet in height and width, and can weigh in the neighborhood of about 2000 pounds. The large size of traditional CT scanners allows for examination of all parts of a subject, such as a human body, from the feet, to the abdomen, to the head. The large size of traditional CT scanners is also a by-product of the need to reduce as much as possible (or eliminate) any relative vibration or movement between the subject being scanned and the traditional CT scanner. That is, traditional CT scanners are purposely built to be bulky. This "bulk" is advantageous for traditional CT scanners as it contributes to their steadiness, and therefore, their ability to avoid/mitigate vibration and motion artifacts that can significantly degrade the quality of a CT scan image.

Also as a result of the size and fixed-site use limitations of traditional CT scanners, is the need to transport patients that are to undergo a CT scan to a CT scanner/dedicated CT scanning room. For example, in a hospital setting, where the subject to be CT scanned is a patient, that patient is moved from his/her patient room to the aforementioned, dedicated CT scanning room. It can be appreciated that many patients may be physically connected and bound to certain monitoring equipment resident in the patient room, e.g., an intravenous (IV) delivery system, various monitors/devices for tracking the patient's vital signs, etc. Transportation of such a patient to a dedicated CT scanning room can be challenging/tedious at the least, requiring, for example, the removal of the patient room connections to devices, the traversal of hospital grounds, and possible reconnection of the patient to monitoring devices in the dedicated CT scanning room. While acceptable in some situations, e.g., when a patient is not on life support or in medical distress, there are other scenarios where transporting the patient can be life-endangering. An example is critically ill patients in a hospital's Intensive Care Unit (ICU). These patients are often connected to nearby equipment through tubes and wires providing life support and monitoring functionality. Transporting these patients to a fixed-site use CT scanner is not only time consuming, but potentially dangerous. Again, to move a critically ill patient from the ICU to a dedicated CT scanning room, medical staff must reconfigure the life support and other equipment for mobile operation, since the patient often must remain tethered to at least the life support equipment. Furthermore, the mobile life support equipment must be on and operating at all times with no interruption. It can be very difficult to mobilize this equipment for such transport. Multiple studies have been conducted to investigate the safety of transporting ICU patients. In one study, about 15% of all transports from the ICU to the radiology department (that include dedicated CT scanning rooms) result in some sort of negative incident, such as interruption of electrical power/or other delivery mechanism via electrical cables and gas supply lines, and other equipment malfunctions. There is also an inherent risk of pathogen exposure to a patient being transported from a safe and sanitized room, through, e.g., less sterile areas of a hospital (elevator, hallway, etc.).

Another example evidencing the risks associated with traditional CT scanners, is in the context of treating stroke patients. Approximately 80% of all strokes are ischemic, where a blood clot or other material blocks an artery in the brain. The standard treatment for ischemic strokes is to give the patient a drug that dissolves blood clots, such as a tPA (tissue plasminogen activator), within the first few hours of noticing symptoms indicative of a stroke. However, the remaining 20% of strokes are hemorrhagic, where a broken blood vessel is bleeding into the brain. Inadvertently administering tPA to such patients will worsen their condition and can result in death. It is therefore critical to determine if a stroke patient is experiencing bleeding in their brain before any medical treatment can be given. A CT scan is quick and effective in detecting bleeding in the brain, and is typically the first step for patients with stroke symptoms. However, problems arise when the patient is not near a hospital with CT scanning capabilities. Without a CT scan to detect brain bleeding, medical personnel can do little, but transport the patient to a CT scanning facility as quickly as possible. This delay in treatment could adversely affect the patient's outcome, expressed in the medical adage, "time is brain."

As noted above, more than 100 million medical CT examinations are performed worldwide, each year. Approximately 15% of these CT examinations are focused on a patient's head or cranial region, and are used to diagnose tumors, bleeding, skull fractures and other, sometimes, life-threatening disorders. Transportable CT scanners, primarily used for head scanning, were thus introduced to partially overcome the above-described patient transport problems. Some transportable CT scanners are approximately five feet in height, and 950 pounds, which while giving them a smaller footprint than a traditional, fixed-site use CT scanner, is nevertheless still a large, and cumbersome device to maneuver and use.

A transportable CT scanner can be mounted on wheels to move the transportable CT scanner across level surfaces, e.g., hospital floors, en route from a radiology equipment storage area to a patient's room. Examples of transportable CT scanners include, e.g., the Neurologica CereTom® head CT scanner, and the Siemens SOMATOM® head CT scanner. Such transportable scanners can be brought to the patient, eliminating the need to transport the patient from their room to a dedicated CT scanning room. These transportable CT scanners can also be installed in ambulances to allow patients to begin treatment at a considerable distance and time away from the nearest hospital.

However, problems still exist with transportable CT scanners. For example, and as alluded to above, transportable CT scanners incorporate wheels to facilitate movement of the transportable CT scanners. However, given their size and weight, the incorporation of wheels in transportable CT scanners is akin to incorporating a somewhat scaled-down traditional CT scanner with a motorized forklift. That is, transporting a transportable CT scanner is still a cumbersome affair that takes time. In fact, the time needed to move a patient from his/her patient room to a CT scanner is merely replaced by the time needed to move a transportable CT scanner to the patient, and as already discussed above, time can be of the essence when treating certain patients/conditions.

In addition to the continued problems with timing, and although a transportable CT scanner can be transported, use and operation of a transportable CT scanner is still cumbersome. For example, once an operator has wheeled a transportable CT scanner to a patient room, the operator must still survey the layout of the patient room and position the transportable CT scanner to the head of the patient's bed. The floor of the patient room must be checked for any obstructions. The headboard of the patient's bed must be removed. The typical transportable CT scanner requires at least 4 feet of room between the head of the patient's bed and any wall/surface (to accommodate the physical size/movement of the transportable CT scanner). Sometimes, the patient's bed must still be moved or repositioned in order to accommodate the transportable CT scanner. Space must be available at the head of the patient's bed to allow the operator to physically move and position the transportable CT scanner next to the head of the bed, and in some cases, physically clamp the transportable CT scanner to the bed. The patient's entire body must then be lifted and slid toward the head of the bed, a distance of 3-4 feet, until the patient's head is within the scan tube/area (bore) of the transportable CT scanner. Sliding the patient is typically done by several staff members pulling the sheets the patient is resting on. Only then, can a CT scanning procedure begin.

As can be appreciated, traditional fixed-site use and transportable CT scanners are a significant expense and require sufficient space for their use. Oftentimes, smaller medical facilities do not have the capability to store and operate a CT scanner. As a result, patients that are treated at these small facilities may need to be transported several hours away to a larger hospital with CT imaging functionality. As described above, this transport can be associated with significant risk for the patient.

FIG. 1 illustrates an example transportable CT scanner 102 as compared to an average human 101. As mentioned above, transportable CT scanner 102 may be approximately five feet high and 950 pounds. CT scanner 102 is mounted on wheels, not visible in FIG. 1, for transport. As mentioned above, the bulkiness of transportable CT scanners, such as transportable CT scanner 102, is such that an operator, e.g., human 101, needs motive assistance akin to a motorized forklift, to move and maneuver transportable CT scanner 102. Additionally, the size/weight of transportable CT scanner 102 means that even though transportable CT scanner 102 can be moved/manipulated by a single operator, such movement/manipulation tends to be slow and awkward, which can be detrimental to a patient's outcome. Even if a transportable CT scanner, such as transportable CT scanner 102 could be moved without motive/motorized assistance, an operator would not be able to easily maneuver transportable CT scanner 102 given its weight.

Figure 2:
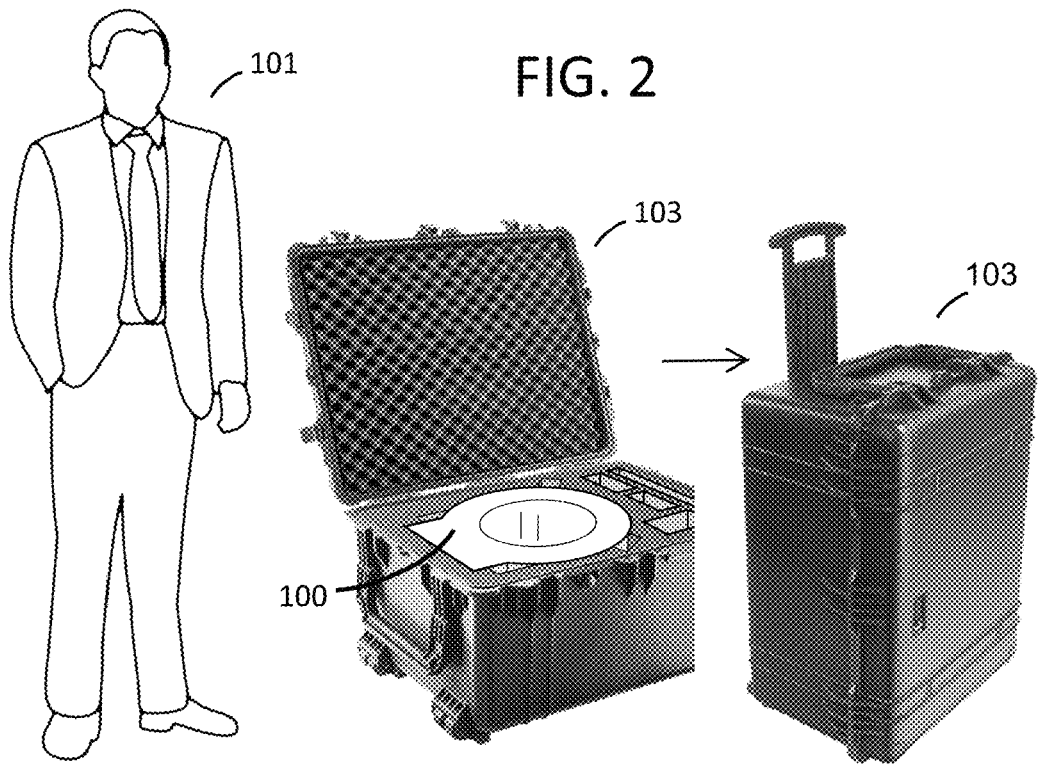
FIG. 2 illustrates an example configuration for transporting an imaging system in accordance with some embodiments.

In contrast, and as discussed above, embodiments of the present disclosure are directed to a truly portable head CT scanner that is sized to allow for unassisted transport to a subject. FIG. 2 illustrates a portable CT scanner 100 in accordance with some embodiments of the present invention, shown in its stowed/stored state in carrying case 103. FIGS. 1 and 2 are illustrated close to scale to demonstrate the relative size of an example portable CT scanner configured in accordance with embodiments of the disclosed technology compared to a traditional transportable CT scanner. This relative size is indicative of the transport issues previously described. Portable head CT scanner 100 is much smaller and more compact, allowing it to be transported in a carrying case 103 that can be manually carried/wheeled by a single person, also referred to as being hand-movable. It should be understood that although an advantage of embodiments of the disclosed technology is the ability to be transported/manipulated manually, embodiments are not necessarily limited to non-automated embodiments in terms of carry/transport of the portable CT scanner.

In some embodiments, portable head CT scanner 100 can be transported in a carrying case such as a conventional hard-sided/padded transport case, an example of which is a Pelican™ case. Portable head CT scanner 100 can fit in a case with interior dimensions of approximately 28"×22"×15", with wheels and handles allowing the case 103, with the portable head CT scanner 100 stowed therein, to be moved and carried by one person. The interior of these cases can comprise conforming foam protectors to cushion portable head CT scanner 100 and various accessories. Fully packed, case 103 and portable head CT scanner 100 can weigh as little as eighty pounds. It should be understood that dimensions or physical characteristics of portable head CT scanner 100 and/or any case/transport medium in which portable head CT scanner 100 may be stowed, e.g., case 103, can vary. However, regardless of the actual weight of carrying case 103 and portable head CT scanner 100, weights that exceed eighty pounds, e.g., one hundred pounds, is still an order of magnitude less than a transportable CT scanner weighing nearly one-half ton. Moreover, the size of portable head CT scanner 100 negates the need for any sort of dedicated/specialized room or environment in which it is to be operated. Options for storing portable head CT scanner 100 while in carrying case 103 are also much greater than those available for traditional CT scanners/transportable CT scanners. That is, portable head CT scanner 100 while in carrying case 103 can be placed in a vehicle trunk, under a desk, in a corner of a room, etc.

Figure 3:
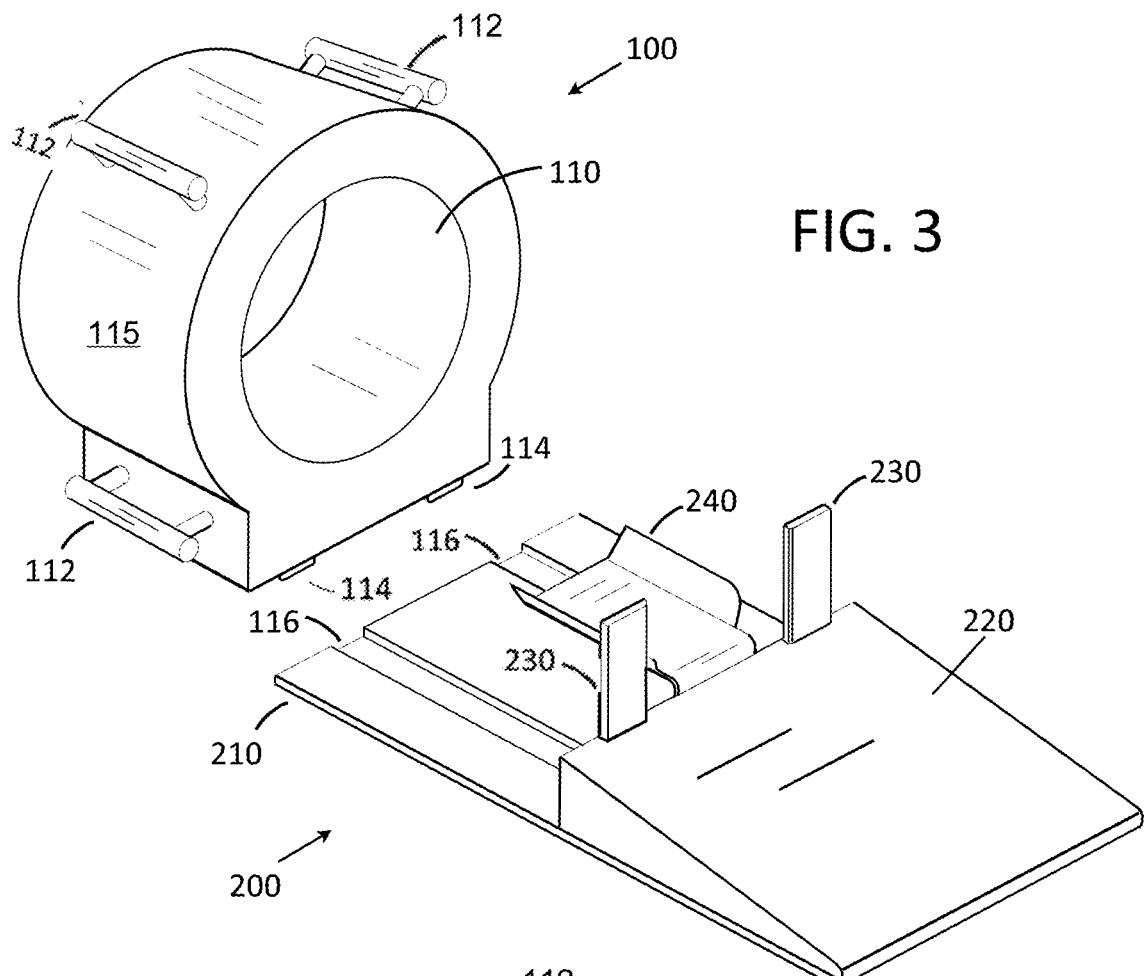
FIG. 3 illustrates an example CT scanner as it connects with a scan board, in accordance with one embodiment.

FIG. 3 illustrates an example portable head CT scanner 100 and scan board 200, in accordance with one embodiment. Head CT scanner 100 can be configured to rest on scan board 200. In some embodiments, scan board 200 may comprise a base 210. Base 210 may comprise a bottom surface and a top surface. Integrated into the top surface are tracks or alignment grooves 116 to receive head CT scanner 100. Tracks 116 may be rectangular in shape and cut into the top surface. Tracks 116 may run parallel to one another and along the length of scan board 200 to facilitate movement of portable head CT scanner 100 along the scan board 200 to position the portable head CT scanner 100 over the patient's head. It should be understood that the example shape/orientation/location of alignment grooves 116 and alignment bars 114 (described below) can vary. One of ordinary skill in the art would understand that different types of alignment grooves/bars can be implemented in accordance with various embodiments so long as alignment bars 114 and alignment grooves 116 can mate such that the desired movement relative to one another is achieved. For example, (although not shown), the entire base of portable head CT scanner 100 may act as a single alignment bar/element that could move along a corresponding/matching alignment groove(s). Base 210 can be made of metal, wood, plastic or some other, similar rigid material(s). In one embodiment, base 210 can measure approximately 20"×48"×0.2" and weigh about 5 pounds. Alignment bars 114 on portable head CT scanner 100 can slide into and along tracks 116 to operatively attach or mount portable head CT scanner 100 to base 210.

Alignment bars 114 in the illustrated example of FIG. 3, may comprise protrusions extending outwards from the bottom of portable head CT scanner 100. As noted above, variations regarding the shape/size/orientation of alignment bars 114 and alignment tracks 116 can vary, but generally, the width and depth (or at least the width) of alignment bars 114 "match" the width/depth of alignment grooves 116. As one of ordinary skill in the art would understand, matching in this context may mean that the width of alignment bars 114 is slightly less than the width of alignment grooves 116 thereby allowing portable head CT scanner 100 to slide within alignment grooves 116. In one embodiment, alignment bars 114 comprise rectangular blocks that fit into tracks 116 so that head CT scanner 100 sits level on scan board 200. In some embodiments, instead of alignment bars, portable head CT scanner 100 may be outfitted with casters, rollers, or wheels that engage with/roll within alignment grooves 116. It should be noted that the dimensions of alignment bars 114 and alignment grooves 116 can vary to effectuate a desired resistance/provide a desired level of friction so that extension/retraction of portable head CT scanner 100 and scan board 200 can be controlled as desired. For example, closer dimensions can result in a "tighter" engagement between alignment bars 114 and alignment grooves 116 making movement harder, but making fixing the position of portable head CT scanner 100 relative to scan board 200 easier.

Scan board 100 may further comprise a support 220. Support 220 can comprise an inclined or canted plane or substantially planar surface, mounted atop or integrated into base 210 to support a patient's torso. In one embodiment, as illustrated in FIG. 3, the incline of support 220 is such that a first portion or end of support 220 nearer to portable head CT scanner 100, when mounted to base 200, is elevated relative to a second portion or end distal from the first portion/end. In this way, an operator can slide scan board 200 underneath the shoulders/torso of a subject, such as a patient. The inclined/canted shape of support 220 tilts or angles the patient's torso upwards and away from a surface on which the patient is lying. A patient's torso can rest on torso support 220 such that the patient's shoulders meet shoulder stops 230 at the upper end of the inclined plane of torso support 220. Shoulder stops 230 may comprise elements or components such as planks or boards that extend upwards relative to base 210. Shoulder stops 230 position the patient's body such that the patient's head is properly positioned/aligned within a central bore 110 (described below) of portable CT head scanner 100. The angle of incline of torso support 220 can vary. For example, portable CT head scanner 100 may be operative with a plurality of different scan boards 200, where the scan boards 200 may have torso supports 220—with varying degrees of incline, e.g., to accommodate different patients (child versus adult), or to accommodate varying needs of a patient. For example, a particular patient may have limited torso mobility, in which case the angle of incline may need to be less than that which can be used with other patients. In some embodiments, torso support 220 may be an adjustable support to effectuate different angles of incline. It should be understood however, that central bore 110 of portable head CT scanner 100 should be able to slide or be positioned to encompass the head (or other portion) of the patient/subject.

With a patient's shoulders contacting shoulder stops 230, and the patient's torso properly positioned atop support 220, the patient's head can be positioned to rest on head support 240 to stabilize the patient's head. The patient's head can rest in a position that is substantially horizontal and parallel to scan board 200. Again, although embodiments described herein refer to a head support and a portable head CT scanner, embodiments of the disclosed technology can be used for/adapted for use in performing CT scans of objects other than a subject's head.

When a patient's head is resting on head support 240, portable head CT scanner 100 can be moved by hand, or a mechanical actuator, across scan board 200 via tracks 116. A central bore 110 in head CT scanner 100 can receive a patient's head as it rests on head support 240. Central bore 110 may comprise a cylindrical hole or aperture through the center of head CT scanner 100. Central bore 110 can be sized to accommodate a human head such that at least a few inches of working space exists between the entire interior circumferential surface of central bore 110 and the patient's head. As compared to traditional fixed-site and transportable CT scanners, central bore 110 is much smaller and more compact, although dimensions, e.g., diameter, of central bore 110 can vary. As noted above, central bore 110 can be cylindrical such that an X-ray imaging assembly travels in a circle around the patient's head. The cylindrical shape of central bore 110 allows an X-ray assembly to image the patient's head at every angle in an even, circular path. Head CT scanner 100 can surround the patient's head while the imaging X-ray assembly rotates around the head and translates from one end of the head, e.g., the top of the head, towards the chin or neck region of the patient, to image the whole head. Example translational mechanisms are described further below.

Figure 4:
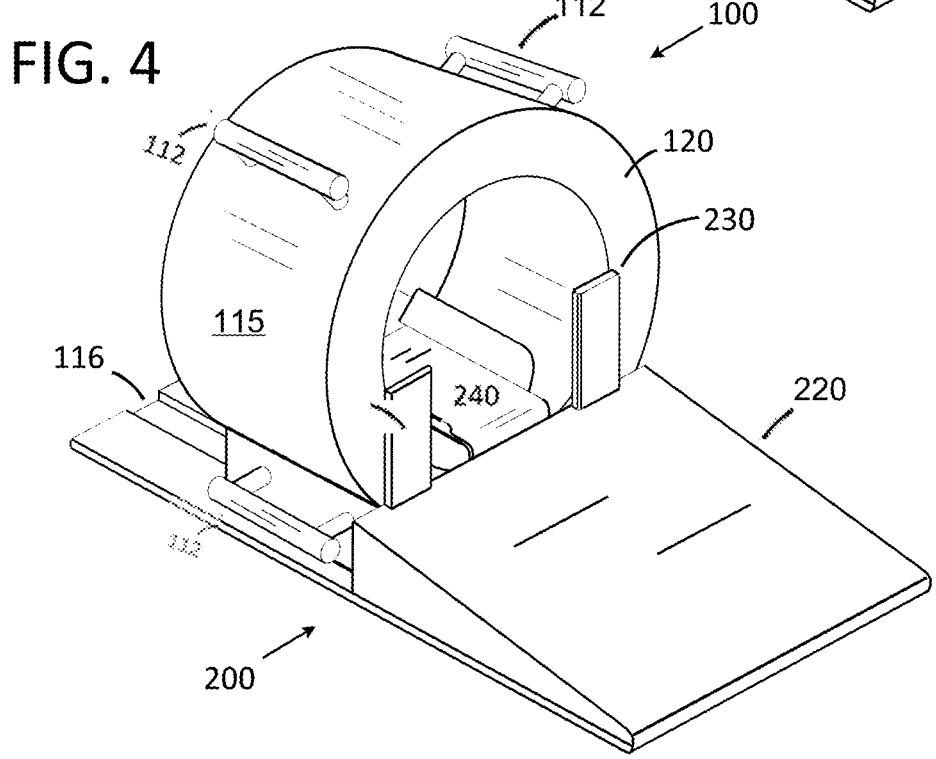
FIG. 4 illustrates the example CT scanner of FIG. 3 while it is connected with a scan board, in accordance with one embodiment.

Portable head CT scanner 100 can be lifted, moved and positioned by handles 112. FIG. 4 illustrates head CT scanner 100 once it has reached the end of alignment grooves 116 and a front face/surface 120 of portable head CT scanner 100 abuts shoulder stops 230/torso support 220. In such a position, portable head CT scanner 100 can fully encompass the patient's head for scanning purposes. Portable head CT scanner 100 can contain elements to acquire CT images, described further below, and can be packaged within a cylindrical enclosure 115 approximately twenty-one inches in diameter and fourteen inches long. In one embodiment, central bore 110 may have an eleven-inch diameter. Handles 112 can be located on sides of the cylindrical enclosure 115 for lifting and positioning the device. Portable head CT scanner 100 may weigh about 40 pounds such that two people can easily lift the portable head CT scanner 100 from its transport case 103 and position it on the scan board 200 (or if the need arises, one person can set up and operate portable head CT scanner 100).

Figure 5A:
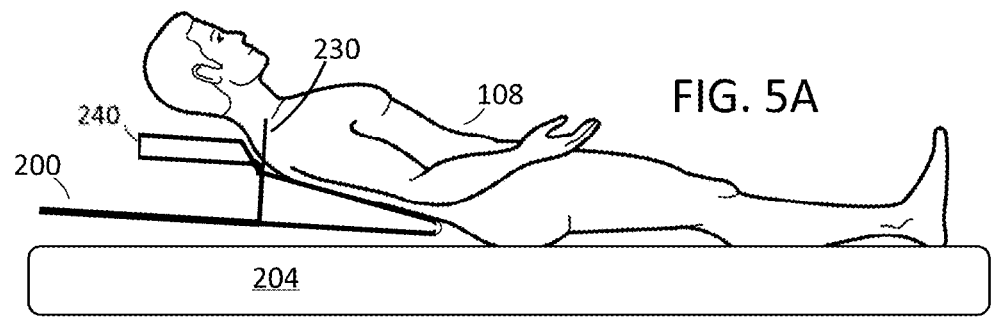
FIGS. 5A-5D illustrate a side view of a human figure as a CT scanner images the human figure, in accordance with one embodiment.

FIGS. 5A-5D illustrate a side view of a patient that is to be scanned using portable head CT scanner 100. It should be noted that some figures may not include all the reference numbers to promote ease of illustration/understanding. As shown in FIG. 5A, patient 108's shoulders may be elevated about 6-8 inches to accommodate scan board 200 being slid (preferably) comfortably under the torso of patient 108. As discussed above, the amount of incline of torso support 220 can vary or can be adjusted. If, for example, the incline plane of torso support 220 has a shorter overall height, then patient 108's shoulders/torso may be elevated a shorter distance. Scan board 200 can be placed under the patient 108's torso with shoulder stops 230 in contact with patient 108's shoulders.

Figure 5B:
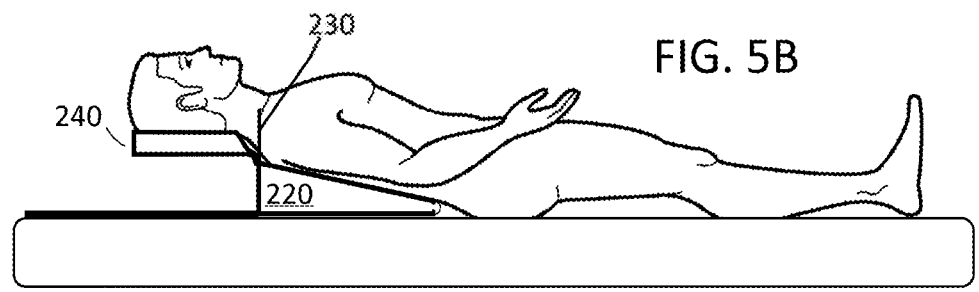

In FIG. 5B, patient 108's torso is lowered until it rests on torso support 220, thereby aligning the torso of the patient 108 with the designated angle defined by torso support 220. Simultaneously, the patient 108's head is lowered to rest on head support 240. Torso support 220 in combination with head support 240 supports the head such that the interior of central bore 110 of portable head CT scanner 100, when attached in the next steps, does not touch the head of patient 108 during imaging. One or more protective guards may be provided to additionally ensure the safety of patient 108, for example, removable plastic guards (not shown) attached to head support 240 to encompass patient 108's head, while being smaller in diameter than the central bore 110. Patient 108's shoulders should remain in contact or near the shoulder stops 230. As mentioned above, scan board 200 can be placed on a patient's hospital bed so that the patient rests in a slightly incline position on the bed. As described above, the patient's head can be parallel to scan board 200 in a horizontal position such that the head is oriented towards the center of central bore 110.

Figure 5C:
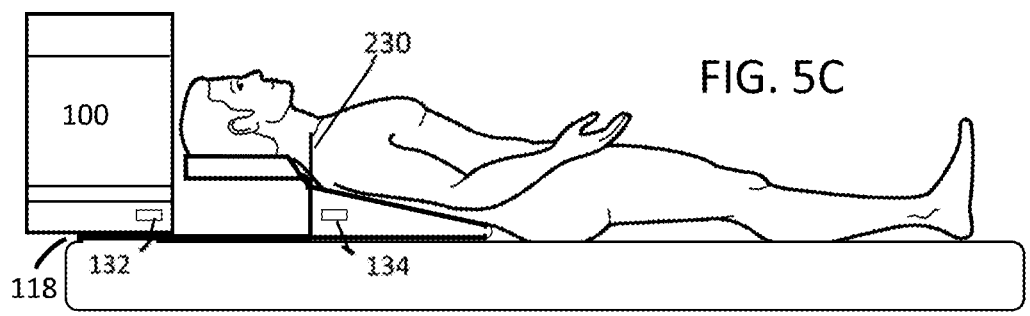

As illustrated in FIG. 5C, portable head CT scanner 100 can be placed on the head end 118 of scan board 200, such that alignment bars 114 mate with alignment grooves 116. In FIG. 5C, portable head CT scanner 100 is positioned at the head end 118 of scan board 200 and does not yet encompass patient 108's head. This position allows patient 108 to become accustomed to the portable head CT scanner 100 before portable head CT scanner 100 is subsequently placed over their head.

Figure 5D:
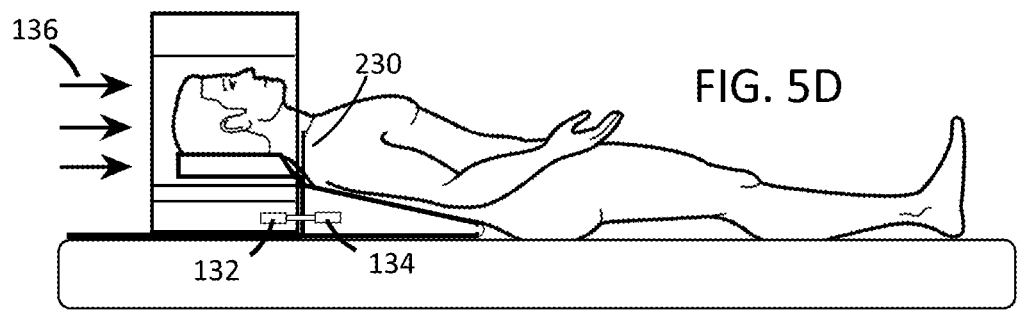

As illustrated in FIG. 5D, portable head CT scanner 100 can be slid/moved (e.g., by an operator/medical staff) to encompass patient 108's head and until its front face 120 is in contact with the shoulder stops 230, e.g., in the direction of arrows 136. This can be facilitated by using alignment grooves 116 with a low-friction surface material, such as Teflon or roller bearings, and can be moved by hand or with the aid of a mechanical translator. Once portable head CT scanner 100 contacts shoulder stops 230, locks 132 and 134 can be engaged to firmly attach head CT scanner 100 to scan board 200. Locks 132 and 134 can be any of the multiple devices used to attach one object to another, such as mechanical clasps, friction devices, electrical actuators, and similar electro-mechanical components. It should be noted that some aspects/elements may not need to be implemented, while in other embodiments other typical aspects/components of a CT scanner may be implemented. For example, shoulder stops 230 may be eschewed, and a surface of torso support 220 orthogonal to base 200 may act as a stop for portable head CT scanner 100. For example, additional locking/positioning elements or mechanisms may be implemented as would be understood by those of ordinary skill in the art.

In some embodiments, front face 120 of portable head CT scanner 100 may stop prior to reaching shoulder stops 230. This positioning may be favorable when only portions of the patient's head are to be scanned. Separate locking mechanisms may be applied to lock head CT scanner 100 at a different position on scan board 200, or locks 132,134 may be operatively implemented on/with portable head CT scanner 100 such that they move with portable head CT scanner 100, and can be engaged at appropriate positions along alignment grooves 116. Portable head CT scanner 100's movement can be guided with alignment grooves 116 (not shown in FIGS. 5A-5D), which can run parallel to the length of scan board 200.

Once in place, portable head CT scanner 100 can acquire a full scan of the brain/cranial region of patient 108 in approximately thirty to sixty seconds. As described above, portable head CT scanner 100 can take images of the human head at various angles (vis-à-vis rotation of the X-ray assembly about a patient's head) and translations (vis-à-vis movement along the alignment grooves 116 or other translational methods described below) to receive a full, three-dimensional view of the scanned area, in this example patient 108's head. The steps or operations in FIGS. 5A-5D can be reversed after the CT scan is complete. Locks 132 and 134 can be disengaged to allow portable head CT scanner 100 to move. Portable head CT scanner 100 can be translated across alignment grooves 116 (not shown in FIGS. 5A-5D) in a direction opposite that of arrows 136 in order to separate or disengage portable head CT scanner 100 from scan board 200. Scan board 200 can be removed from the bed (or applicable surface) to return patient 108 to a horizontal position on bed 204. Portable head CT scanner 100 and/or scan board 200 can be repackaged for transport (e.g. using carrying case 103). In some embodiments, head CT scanner 100 and scan board 200 may be transported separately. This entire setup, scanning, disengagement process can take place over the span of a few minutes.

A key advantage of this embodiment is the reduction of vibration and motion artifacts during the CT scanning. By placing both portable head CT scanner 100 and patient 108 on scan board 200, any incidental motion resulting from the softness of hospital bed 204 will be equally transferred to each of them. Therefore, there is little to no relative movement between patient 108 and portable head CT scanner 100, which stabilizes the X-ray/CT scan imaging.

Typically, a patient's bed is far too soft and unstable for traditional or conventional CT scanning technology. Head CT scanners, including some embodiment of the portable head CT scanner 100, generally reconstruct images with 0.5 mm pixels, meaning that any incidental motion of the CT scanner or patient during the scanning process should be less than this distance for optimal imaging. All present-day medical CT scanners rest upon the floor, providing stability far better than this 0.5 mm requirement. In contrast, embodiments of the disclosed technology rests upon a patient bed's mattress, which can easily result in movements of 5 mm or greater, ten times the 0.5 mm limit. However, embodiments of the disclosed technology are designed with the recognition that the individual motions of portable head CT scanner 100 and a patient are unimportant; only the relative motion between the two matters. This motion problem is solved by providing another component, scan board 200, to which the portable head CT scanner 100 connects, and to which patient connects, in order to eliminate any relative motion. Even though portable head CT scanner 100, scan board 200, and the patient will undoubtedly move together as a group up to 5 mm, the relative motion between portable head CT scanner 100 and the patient is reduced below the 0.5 mm threshold.

FIGS. 6 and 7 illustrate an example head CT scanner separated into various components. Here, the "front" of the head CT scanner refers to the side where a subject's head is inserted, with the "rear" referring to the opposite side. FIG. 6 illustrates a rear plate 302, a turntable bearing 304, and a rear bore tube 306. Rear plate 302 can comprise a structural member supporting scanning assemblies. In some embodiments, rear plate 302 comprises a disk portion 302a with a bore 302b corresponding to the central bore 110 of the portable head CT scanner 100, and a base 302c. In one embodiment, the disk 302a may be 20.5 inch in diameter along its outer edge, and a 11.25 inch bore. The shape of rear plate 302 may vary in accordance with various embodiments. Rear plate 302 can be configured such that an X-ray imaging assembly can travel in a circle around, e.g., a human head to take images at different angles. Rear plate 302 may further comprise a rectangular base 302c positioned, in this example, perpendicular to the disk 302a. The rectangular base 302c can be large enough to support the disk 302a, and other components of portable head CT scanner 100. The components of rear plate 302 may comprise, for example, a 0.25 inch thick aluminum (or other sufficiently rigid material) sheet able to support the aforementioned scanning assembly components. Rear plate 302 can comprise various holes or bores in the rectangular base 302c through which various components of portable head CT scanner 100 may be affixed or mounted. These holes are described further below in FIGS. 9-11.

Turntable bearing 304, also known as a slew bearing, can be affixed to a front-facing surface of disk 302a, concentric with bore 302b of rear plate 302 (as partially indicated by the broken lines in FIG. 6 showing how the exploded-view parts are mated). Turntable bearing 304 can comprise two rings/ringed surfaces, separated by a multitude of ball bearing, allowing the two rings to rotate relative to one another. In the embodiment of FIGS. 6 and 7, the slew ring 304 comprises a rear ring 304a, which forms the rear surface of slew ring 304, and a front ring 304b which forms the front surface of slew ring 304. The rear ring 304a and the front ring 304b are separated by a multitude of ball bearings (not shown in FIGS. 6 and 7), thereby allowing them to rotate freely relative to each other. While slew bearing 304 is shown as a single object in FIGS. 6 and 7, this is only for simplicity of illustration and it is to be understood that slew bearing 304 comprises rear ring 304a, front ring 304b, and the multitude of ball bears, thereby allowing rear ring 304a and front ring 304b to rotate independently. Other configurations of slew bearings are possible and commercially available. For example, some slew bearings comprise an outer ring and an inner ring disposed within the circumference of the outer ring, with ball bearings held therebetween, thereby providing the same function of allowing one surface to rotate freely from another surface. One of ordinary skill in the art would understand how to affix elements of portable head CT scanner 100 to each of the various slew ring embodiments, be they comprised of movable front and rear surfaces, inner and outer rings, or other configurations.

As illustrated in FIG. 7, the rear ring 304a of slew bearing 304 can be affixed to the front facing surface of rear plate 302 by industrial adhesive or bolts (not shown), while the front ring 304b of slew bearing 304 can be affixed to rotating plate 340. Turntable bearing 304 can comprise one or more holes disposed at various locations around the respective rings to receive screws or other adhesive materials. The connection between rear plate 320 and slew bearing 304, and the connection between rotating plate 340 and slew bearing 304, thereby providing a rigid connection between rear plate 320 and rotating plate 340 in all directions and axes of motion, except allowing the freedom to rotate around the central axis of the bore 110.

As also shown in FIGS. 6 and 7, rear bore tube 306, with an outside diameter of 11.25", may be inserted and attached/mounted into the 11.25" diameter bore 302b of rear plate 302 (as indicated by the broken lines in FIG. 6 showing how the exploded-view parts are mated). In some embodiments, rear bore tube 306 may be five inches long and formed from 0.125" thick aluminum. Rear bore tube 306 can be attached to effectuate a safety barrier between the patient and the moving assemblies within the portable head scanner 100. A rear bore tube 306 outside diameter of 11.25", with a wall thickness of 0.125," results in an inside diameter of 11.0", where the patient's head must be inserted. Other diameters can also be provided as needed for different sizes of patients, such as adults versus children. The rear bore tube 306 can be various lengths to accommodate the imaging of different size (length) heads or for different scanning purposes. For example, portable head CT scanner 100 may be limited to imaging the top part of the human head, in which case, rear bore tube 306 may be shorter in length when compared to a rear bore tube used to image the entirety (top to chin/neck) of the head.

FIG. 7 illustrates portable head CT scanner 100 with rear plate 302, turntable bearing 304, and rear bore tube 306 in an assembled state. With these components assembled, rotating plate 340 can be attached or mounted to front ring 304b of turntable bearing 304. Rotating plate 340 can comprise a rigid material such as aluminum, steel, or plastic. The material of rotating plate 340 may be the same as that of rear plate 302, but can be different as well. Rotating plate 340 may be approximately twenty inches in diameter and 0.25 inches thick. In the center of rotating plate 340, an interior bore 340b is provided with a diameter slightly larger than the outside diameter of the rear bore tube 306, allowing the rear bore tube 306 to pass through bore 340b without contacting bore 340b. This allows rotating plate 340 to turn freely, while the rear bore tube 306 remains stationary, as needed to provide a safety barrier for the patient. Rotating plate 340 can be mounted to turntable bearing 304 through bolts, one of which is labeled 341 (for ease/clarity of illustration, only one of such bolts is labeled) or other means, again, allowing it to rotate freely with respect to rear plate 302. Rotating plate 340 can be driven by a motor or may comprise various types of flexible belts and ring gears to facilitate such rotational movement. In the example of FIG. 7, rotating plate 340 and ring 304b of turntable bearing 304 are shown to be capable of rotating in a clockwise direction; however, this assembly can rotate in one or more directions as necessary to image all areas of the human head (or other subject). Rotating plate 340 may change directions of rotation during imaging to capture/recapture images of certain areas of the head/subject. For example, the X-ray assembly may re-image sections on the human head for clearer images.

Attached to rotating plate 340 is X-ray source 350 and X-ray detector 360 in precise alignment. Secondary components of the X-ray imaging system are also mounted on rotating plate 340 but are omitted for clarity. These may include: a computer processor for control and data acquisition, a battery for powering the various components, a motor for turning rotating plate 340, a Wi-fi or other radio communication link for receiving and sending digital data and control signals outside the rotating plate, and similar devices commonly associated with CT scanners. As can be appreciated, the space available for X-ray source 350 is very limited in a portable head CT scanner 100, limiting the amount of its operating power, and therefore the amount of power it requires. One embodiment of the portable head CT scanner 100 requires only 120 watts of power during operation, hundreds of times lower than traditional fixed-site CT scanners, and ten times lower than transportable CT scanners. This low power consumption allows the portable CT head scanner to operate from on-board batteries, or at least smaller batteries, than traditional CT scanners. In the example of FIG. 7, X-ray source 350 can comprise a known or later-discovered/developed X-ray emitting device operated with appropriate electronic and mechanical components, and capable of or adapted to conduct CT imaging.

Figure 8:
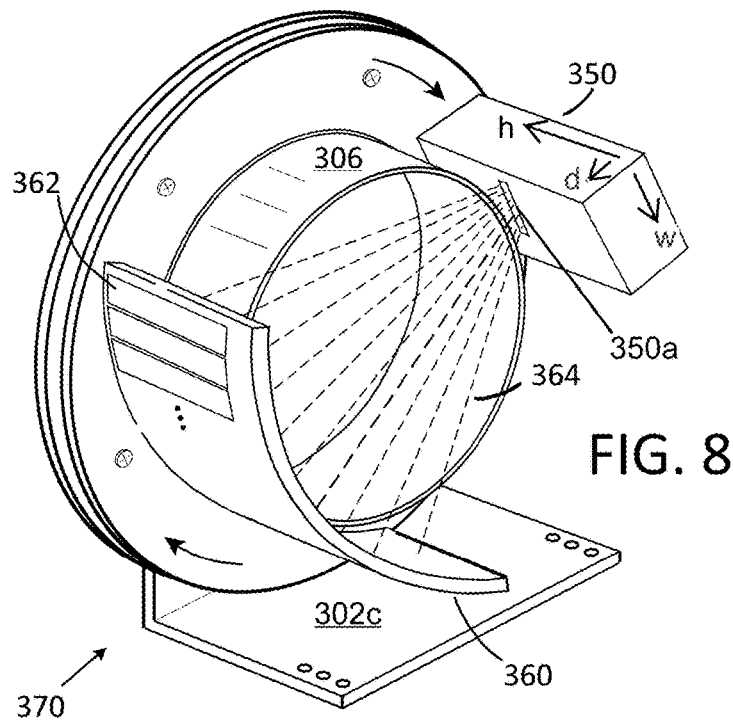
FIG. 8 illustrates an X-ray detector and X-ray source as implemented with a CT scanner in accordance with some embodiments.

FIG. 8 illustrates that X-ray source 350 may have a collimating aperture 350a through which the X-rays generated by X-ray source 350 can propagate toward X-ray detector 360. X-ray detector 360 can comprise a curved or arc'ed rectangular sheet that follows the curvature/arc'ed shape of rotating plate 340. The surface of X-ray detector 360 facing X-ray source 350 can comprise one or more detector cards (one of which is labeled as detector card 362). These detector cards can comprise appropriate X-ray detection components or devices that can receive the X-rays, in this example, an X-ray fan beam 364 that pass through a subject being scanned. X-ray detector 360 may change in size, shape, or curve to match changes in the size of rotating plate 340.

FIG. 8 further illustrates a completed assembly that comprises the inner "workings" of portable head CT scanner 100. As illustrated in FIG. 8, the X-ray source 350 may transmit an X-ray fan beam 364 to be received/detected by X-ray detector 360. In one embodiment, X-ray source 350 may have the following dimensions 5.5 inches "wide"×3.5 inches "deep"×10 "high," and may operate at approximately 120 KV and 1 ma. The "spread" of X-ray fan beam 364 has an approximate width of ninety degrees and an approximate "thickness" (in the "h" direction) of five degrees. X-ray fan beam 364 can illuminate the active area of X-ray detector 360 with an approximate curved width of 20 inches and a height of 1.4 inches. In some embodiments, X-ray detector 360 can comprise a two-dimensional array of approximately 500 pixels by 32 pixels, with each pixel having a size of approximately 1×1 mm. X-ray detector 360 can be formed from individual detector cards 362. The end quarter of the X-ray detector cards may be removed to reduce the width of the fan beam. This can be useful in some cases to reduce the X-ray dose to the surface of the head/subject. X-ray fan beam 364 can be further adjusted using a computer-controlled collimator (not shown), to adjust the thickness of X-ray fan beam 364.

Traditional CT scanners use filtered-backprojection (FBP) to convert the raw data (attenuation measurements) from the X-ray source and X-ray detector into the final CT scan images. FBP comprises analytic algorithms that efficiently reconstruct an image. However, FBP requires the raw data to be in a specific format. For example, the X-ray detector must be curved in a semicircle fashion, and centered on the X-ray source. Likewise, the X-ray focal spot and each detector element of the X-ray detector must be represented as an infinitely small point, not the typical 1×1 mm area that the detector elements/pixels actually are. Spacing constraints in a small scanner do not permit a traditional geometry to be used. However, this can be overcome through the use of iterative algorithms, such as the algebraic reconstruction technique (ART). Unlike FBP, iterative algorithms are very tolerant of non-traditional X-ray imaging geometries and can account for secondary factors such as X-ray beam profile. Iterative algorithms have seldom been used (if at all) in the CT scanner context because of their long execution time. However, they are now practical for some scanners with the use of high-speed computing platforms such as Graphical Processing Units (GPU).

The compact size of the portable body scanner 100 limits the space available for X-ray source 350, which in turn, limits its maximum operating power. Traditionally, this can reduce the resulting image quality. Embodiments of the disclosed technology can be limited to an X-ray power of about 120 watts (1 ma at 120 KV). For comparison's sake, transportable CT scanners produce high quality images of the brain by operating at 1,000 watts (8 ma at 120 KV). This power level requires transportable CT scanners to weigh 950 pounds (i.e., the componentry required to generate/deliver the requisite power). In contrast, embodiments of the disclosed technology only weigh about 40 pounds, corresponding to a maximum X-ray power of 120 watts.

To be effective, embodiments of the disclosed technology should produce at least the same image quality as traditional/transportable CT scanners, while only using one-eighth the X-ray power. More specifically, the image quality produced by a CT scanner is primarily determined by the number of X-rays received by the X-ray detector. In the portable head CT scanner 100, the eight-fold lower X-ray power results in an eight-fold lower generation of X-rays. In itself, this would result in an eight-fold lower number of X-rays received by the X-ray detector, and the corresponding reduction in image quality. However, the portable head CT scanner 100 compensates for this by providing more than an eight-fold improvement in the collection of X-rays generated by the X-ray source, thereby providing the same number of X-rays received at the detector, and an equivalent image quality as other CT scanners. This is possible because the number of X-rays received by the X-ray detector is inversely proportional to the square of the distance between the X-ray source and the X-ray detector, commonly called the SID (source-image-distance). The SID associated with embodiments of the disclosed technology is about 14 inches, compared to 23 inches for, e.g., a transportable CT scanner. Again, the number of X-rays at the X-ray detector is inversely proportional to the square of the SID, meaning that embodiments of the disclosed technology are $(23/14)^2=2.7$ times more efficient in collecting the X-rays generated by the X-ray source.

Another way that embodiments of the disclosed technology overcome the power problem is by using an X-ray detector that is wider in the direction perpendicular to the direction of travel of the X-ray fan beam. While a traditional transportable CT scanner may use, e.g., a 10 mm-wide detector, embodiments of the disclosed technology may use a 35.8 mm-wide device, resulting in the X-ray detector collecting a factor of $(35.8/10)=3.58$ more of the X-rays generated by the X-ray source. Combining the factor of 2.7 from the shorter SID, with the factor of 3.58 from the wider X-ray detector, embodiments of the disclosed technology collect $(3.58/10)=9.7$ times more of the X-rays generated by the X-ray source. This more than compensates for the eight-fold lower power of the X-ray source 350, allowing the disclosed embodiments to produce the same image quality of other CT systems.

Yet another factor is considered by embodiments of the disclosed technology. Reducing the SID and increasing the detector width both greatly increase the level of scattered X-rays received by the X-ray detector, which itself causes image degradation. However, as described below, the portable head CT scanner 100 further provides for the elimination of the effects of this scatter, thereby retaining the required image quality. These three factors of lower SID, greater detector width, and scatter elimination (discussed below) therefore may, in some embodiments, work hand-in-hand to overcome the problem of lower X-ray power.

Figure 9:
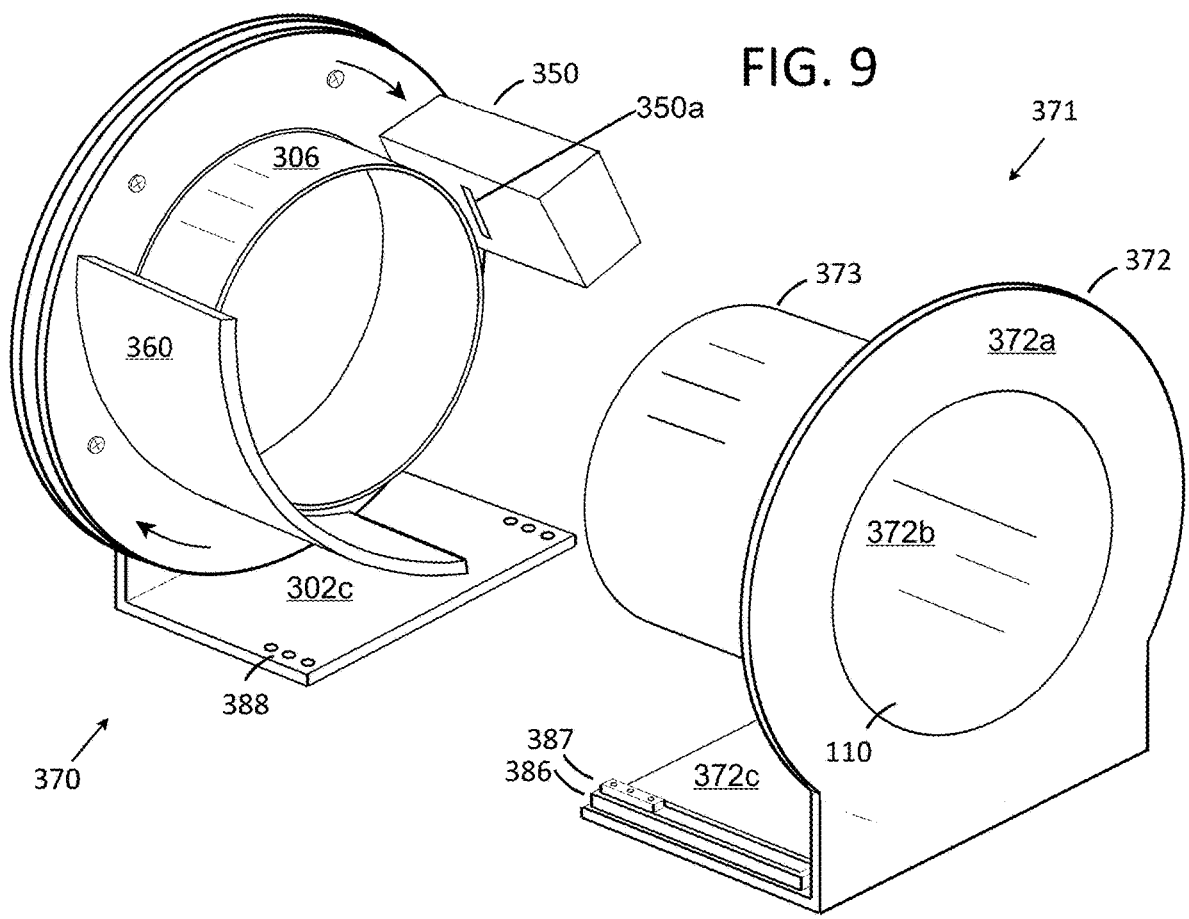
FIG. 9 illustrates a CT scanner with a corresponding cover, in accordance with some embodiments.

FIG. 9 illustrates a rear assembly 370 and front assembly 371 making up portable head CT scanner 100. As described above in FIGS. 6-8, rear assembly 370 can comprise at least rear plate 306, turntable bearing 304, rear bore tube 306, rotating plate 340, X-ray source 350, and X-ray detector 360. Front assembly 370 can comprise a front plate 372 that parallels rear plate 302 except with a slightly larger rectangular base 372c. In one embodiment, front plate 372 comprises a disk 372a with a center bore 372b. Front plate 372 may also have a front bore tube 373. This front bore tube may be fourteen inches long and may tightly fit inside rear bore tube 306 when assembled. Front bore tube 373 can vary in length depending on the subject to be imaged. As described above, it may be desirable to scan a portion of the patient's head in some scenarios, while in other scenarios, scanning the entirety of a patient's head is warranted. Front bore tube 373 can comprise an X-ray transparent material, such as plastic or carbon fiber. In some embodiments, front bore tube 373 may have an overall thickness of about 0.080 inches, although front bore tube 373 can vary in thickness depending on the material. Various materials can be used to facilitate X-ray imaging, and front bore tube 373 may combine any such materials in its composition to allow X-ray fan beams, e.g., X-ray fan beam 364, to pass. The rectangular base 372c of front plate 372 allows it to receive the rectangular base 302c of rear plate 302, described further below.

Two linear actuators 386 can be mounted symmetrically on the sides of the rectangular base 372c of front plate 372 (one is shown in FIG. 9). Electric motors attached to these actuators can cause slides 387 on the linear actuators 386 to move about eight inches under computer control. The distance that slides 387 move can depend on the length of the front bore tube 373 and/or the length/height of the patient's head. Linear actuators 386 can be adjusted to translate different distances in accordance with the desired CT scan procedure. Linear actuators 386 may comprise lead screws, ball screws, and/or belts to translate slides 387. Additional linear actuators, for example located at the sides or top of the front assembly 371, may be provided, for example, for additional mechanical support. A single linear actuator may be used, for example to provide lower cost or reduced size.

Figure 10:
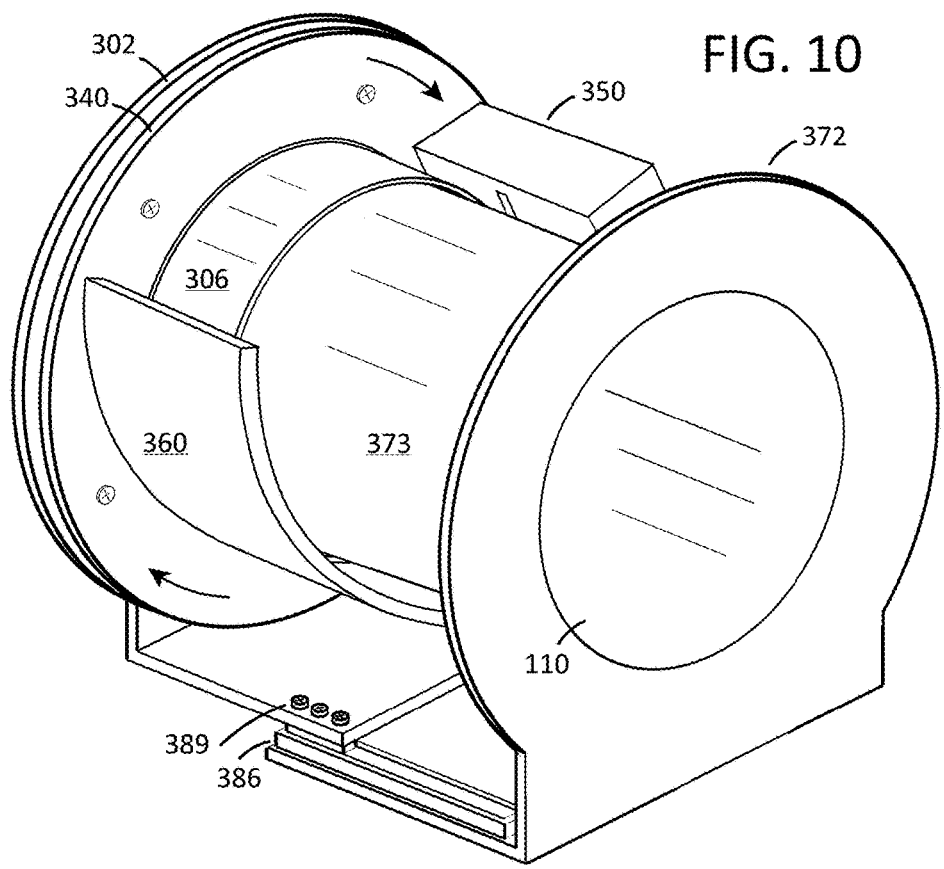
FIG. 10 illustrates a fully assembled CT scanner in an extended position, in accordance with one embodiment.

Rear assembly 370 can comprise various mounting holes (in this example, three) located proximate to the sides of the rectangular base 302c of rear plate 302. Corresponding to these holes are three threaded holes in the slide 387 on front assembly 371. FIG. 10 illustrates how rear assembly 370 can mate with front assembly 371. Connecting bolts 389 can pass through mounting holes 388 and into the threaded holes on slides 387 to lock rear assembly 370 with front assembly 371. Rear assembly 370 can mate with front assembly 371 using different attachment methods or mechanisms. For example, instead of connecting bolts, rear assembly 370 can be locked with front assembly 371 using adhesives or other support structures. As described above, front bore tube 373 can fit tightly inside rear bore tube 306. Front bore tube 373 can be inserted inside rear bore tube 306 to create a bore 110 that passes through the front and rear assemblies.

Figure 11:
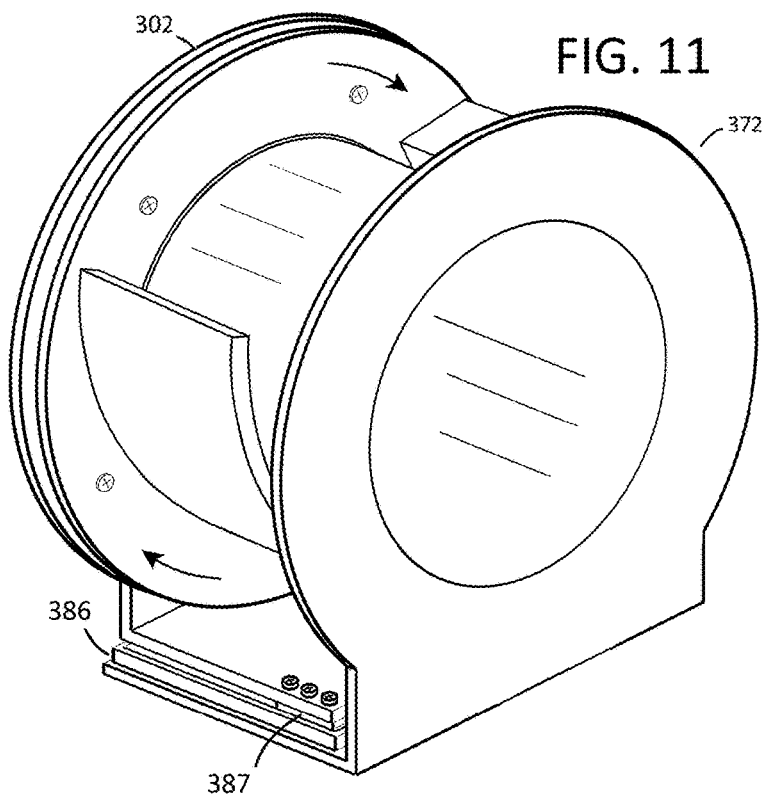
FIG. 11 illustrates a fully assembled CT scanner in a retracted position, in accordance with one embodiment.

FIG. 10 shows an extended position of the apparatus with the rear plate 302 at its farthest from the front plate 372. In some embodiments, the distance between the front plate 372 and rear plate 302 may comprise approximately twenty-two inches in the extended position. As described above, this distance can change depending on the length the X-ray assembly translates to scan the human head. FIG. 11 illustrates portable head CT scanner 100 in a fully retracted position. Here, rear plate 302 is at its closest to front plate 372. In some embodiments, this distance is approximately fourteen inches.

Figure 12A:
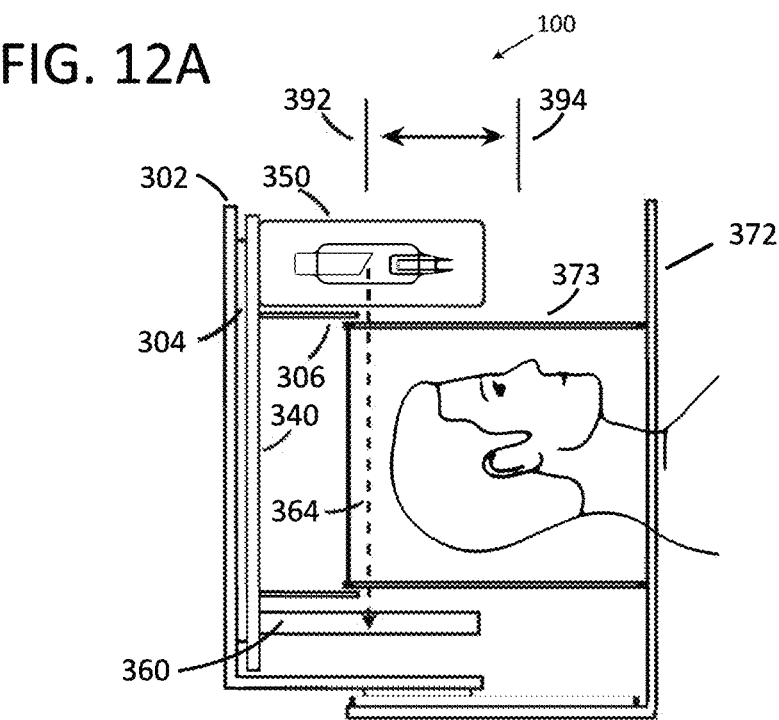
FIG. 12A-12B illustrates side views of the CT scanner as it scans a human head, in accordance with some embodiments.
Figure 12B:
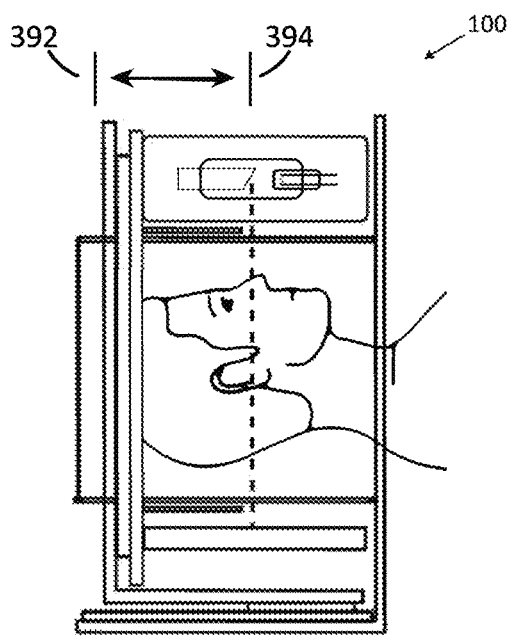

The motion between the extended and retracted positions, provided by linear actuators 386, forms the translational motion of the CT scanning process. By extending or retracting the rear assembly 370, with respect to the front assembly 371, X-ray beam 364 can pass through the entirety of a patient's brain (or other subject/object). This is further illustrated in FIGS. 12A and 12B, showing side views of portable head CT scanner 100 in the extended and retracted positions, respectively. As the apparatus moves from the extended to the retracted position, X-ray beam 364 passes from a first location 392 outside the head, through the head to scan the brain, terminating with the X-ray beam 364 at a second location 394 approximately at the patient's nose. X-ray source 350 is shown in these figures along with a portion of its internal construction in some embodiments, an outer enclosure encompassing an X-ray tube, illustrating the location of the X-ray focal spot.

Figure 13A:
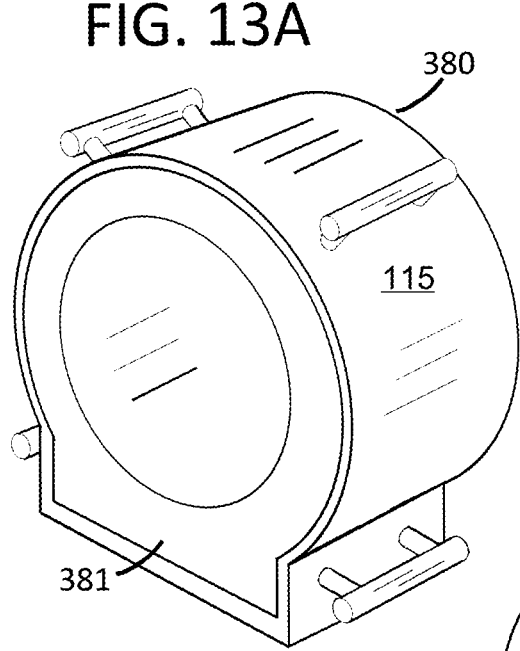
FIG. 13A-13B illustrates example CT scanners as it extends, in accordance with one embodiment.
Figure 13B:
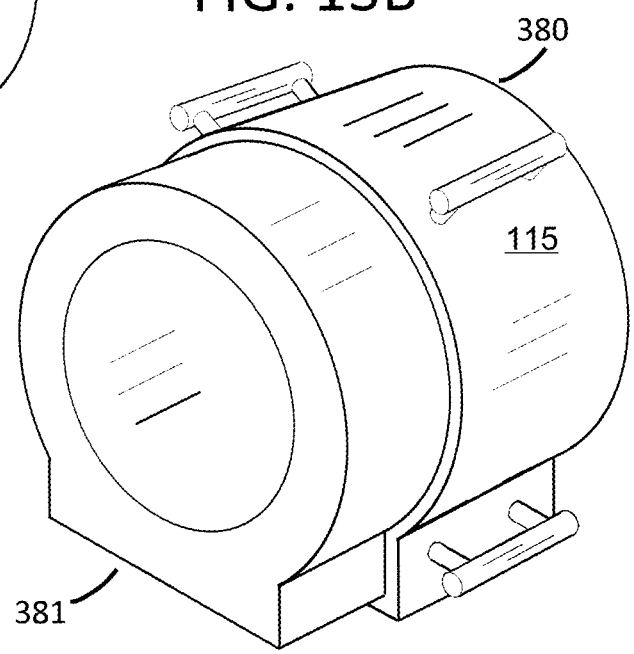

FIGS. 13A and 13B demonstrate the extended and retracted positions of the head CT scanner, respectively, when cylindrical enclosure 115 is attached/implemented. Front assembly 371 and rear assembly 370 may each have additional corresponding covers/enclosures 381, 380, respectively to enclose the components described above and contained therein, as well as to facilitate movement of the assemblies. These covers or enclosures 380 and 381 may comprise various materials for high strength and low weight, such as fiberglass, carbon fiber, or honeycomb materials. Further, enclosures 380 and 381, or a portion thereof, may comprise materials such as lead, tungsten, tantalum, and tin to shield against X-ray leakage. As shown in FIGS. 13A and 13B, on the extension cycle, rear assembly 370 (enclosed by cover 380) telescopes out of front assembly 371 (enclosed by cover 381) by up to eight inches, while still providing a protective cover/enclosure or "outer packaging" between the inner components of the scanner, the patient, and all persons in the vicinity. As known in the art, this translational motion, which is imparted to X-ray fan beam 364 during use, in conjunction with the rotation of the X-ray assembly is sufficient to capture all information needed for CT reconstruction of a three-dimensional image of a patient's brain in a digital computer/with a computer processor.

The embodiments illustrated in FIGS. 6-13 generally relate to a translational mechanism that is fully contained within portable head CT scanner 100, allowing portable head CT scanner 100 to extend and retract to effectuate the translational motion for a CT scanning procedure. Other embodiments are also contemplated, wherein the translational mechanism is partially or fully mounted on a scan board, such as scan board 200. In this way, extension and retraction of portable head CT scanner 100 is avoided. In these embodiments. portable head CT scanner 100 would have a fixed outer housing.

Figure 14:
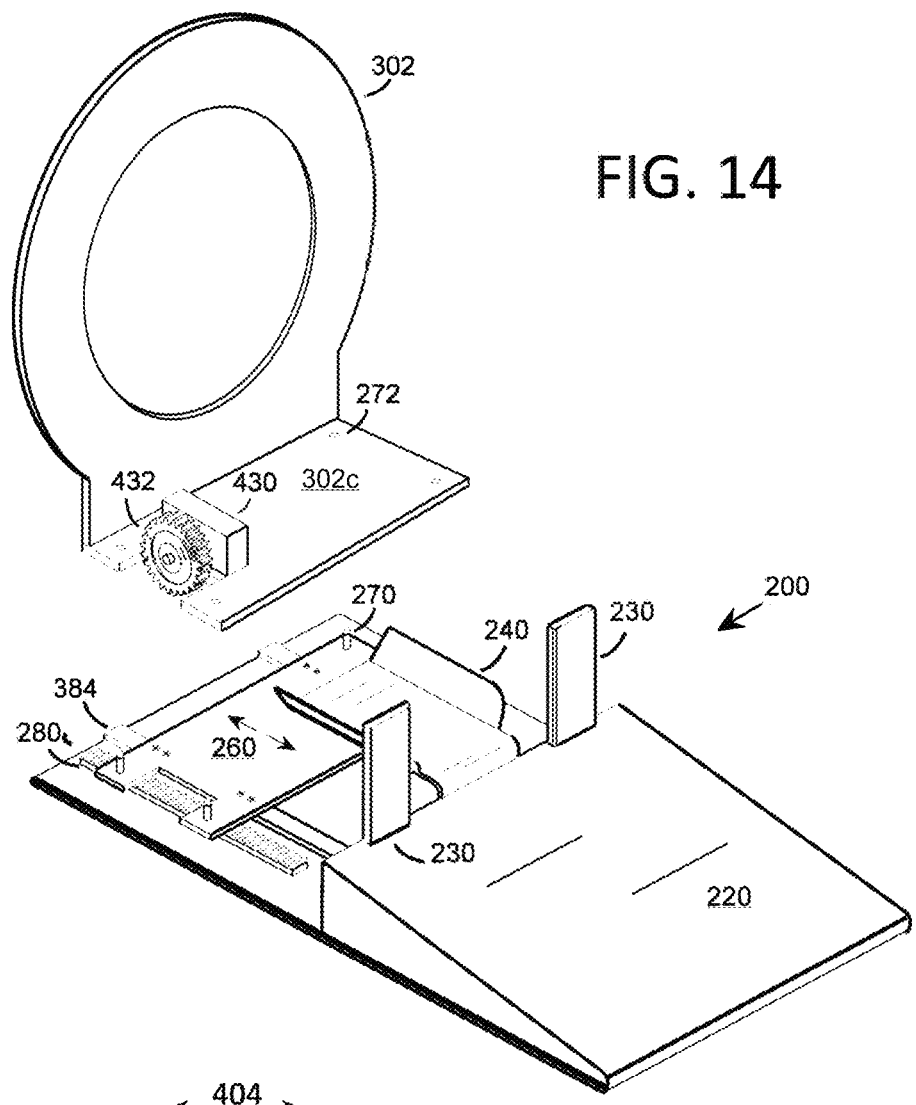
FIG. 14 illustrates an example configuration between the CT scanner and a scan board, in accordance with one embodiment.
Figure 15:
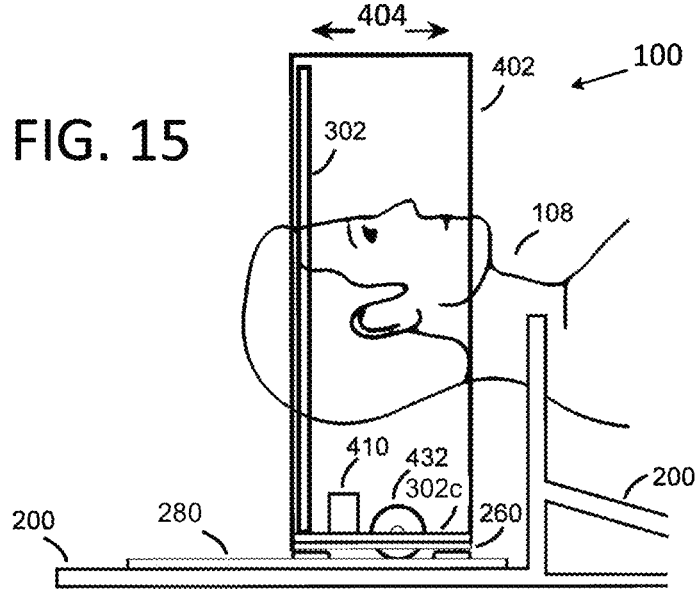
FIG. 15 illustrates a side view of the CT scanner of FIG. 14 as it scans a human head, in accordance with one embodiment.

FIGS. 14 and 15 illustrate such an embodiment, wherein the translation mechanism functionality is split between portable head CT scanner 100 and the scan board 200. For ease of illustration and explanation, only the rear plate 302 of rear assembly 370 is shown. In the example of FIG. 14, a cutout in base 302c of rear plate 302 receives a pinion 432 extending below the bottom surface of the rectangular base 302c. Pinion 432 may comprise one or more wheels or other moving mechanisms that can translate the head CT scanner. Pinion 432 can be driven by a drive motor 430, causing it to rotate at a rate controlled by a system computer. A translational plate 260 can be mounted on two linear slides 384, which in turn are mounted on scan board 200. When portable head CT scanner 100 is mated with scan board 200, holes 272 in the rectangular base 302c of rear plate 302 (e.g., in the corners of the rectangular base 302c) can be placed over alignment pins 270. Alignment pins 270 can be mounted on translational plate 260 to rigidly connect the rectangular base of rear plate 302 to translational plate 260. Translational plate 260 may have a cutout similar to that of the rear plate. The cutouts of each piece can be aligned such that pinion 432 extends through the cutouts and engages with a rack 280 mounted on bedboard 200. Linear slides 384 can comprise roller bearings, ball bearings, low friction materials or other known methods to facilitate easy movement. Therefore, the head CT scanner 100 may be moved along these slides via translational plate 260 by rotation of the pinion 432 and motor 430. Control module 410 can provide the required power, control and communications to operate the motor 430 in providing translation of the portable head scanner 100.

FIG. 15 is a side view of the embodiment of FIG. 14 in a connected/assembled state, additionally showing the perimeter/outline of an outer case/cover/enclosure 402 of portable head CT scanner 100. A control module 410 is additionally illustrated as being mounted to the rear plate 302. This may provide the power, control and communications needed to operate the motor 430 in providing translation of portable head CT scanner 100.

Figure 16:
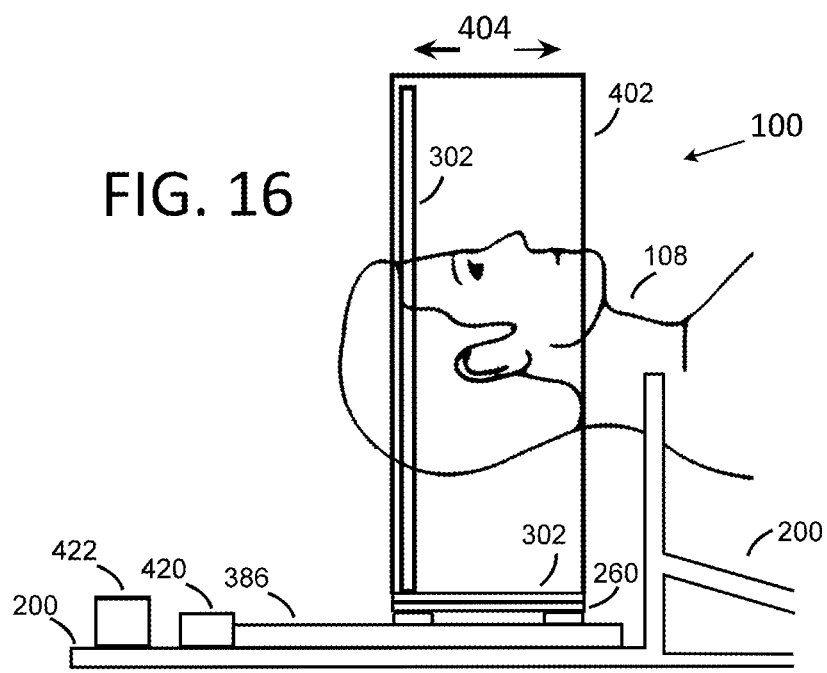
FIG. 16 illustrates a side view of a CT scanner with a translational mechanism contained on the scan board, in accordance with one embodiment.

Another embodiment is illustrated in FIG. 16, wherein the translational mechanism is entirely disposed on scan board 200. Instead of using linear slides 384, translational plate 260 can be mounted on two linear actuators 386 that can provide the functionality of linear slides plus translational force. As illustrated in FIG. 16, one or more motors 420 can be connected to linear actuators 386 to provide the translational movement. Any type of linear actuator or motor can be used to facilitate movement. Linear actuators 386 may move a set distance or may change the distance it moves. Linear actuators 386 may be programmed to move a distance depending on the area being scanned. A control module 422 is located on scan board 200 to provide the power, control and communications needed to operate motors 420 in providing translation of portable head CT scanner 100. Control module 422 may comprise any system to communicate instructions to motors 420 to facilitate movement of linear actuators 386.

Figure 17:
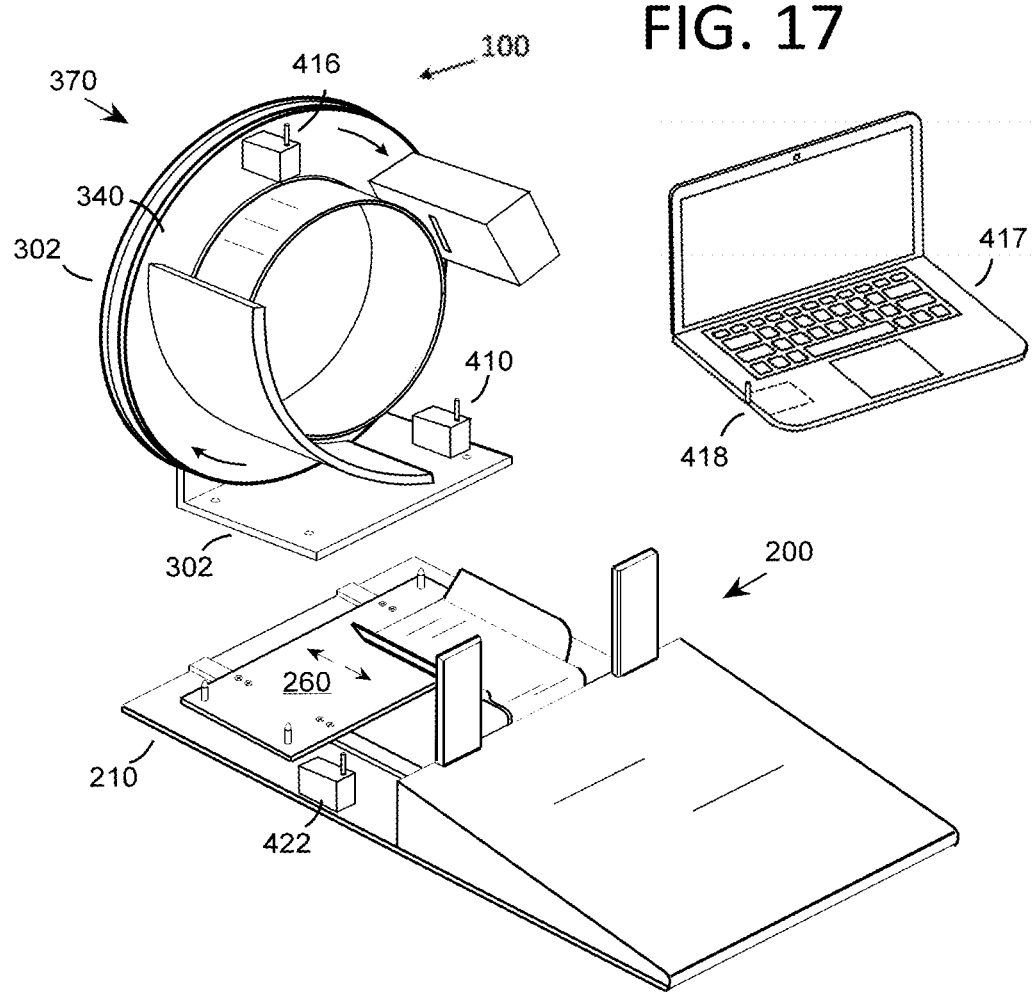
FIG. 17 illustrates an example CT imaging system in accordance with one embodiment.

FIG. 17 illustrates aspects of portable head CT scanner 100 that effectuate wireless communications capabilities. Here, rotating plate 340, rear plate 302, scan board 200, and computer 417 may communicate with each other as needed to synchronize the various components during scanning and transfer the acquired image data. Wireless communication can be achieved with Wi-Fi, Bluetooth, or similar radio/near field/network transceiving. These components can communicate through control modules 416, 410, and 422, with a corresponding laptop communication component 418. This configuration would not require plugin electrical connectors between the separable assemblies, slip ring connectors between rotational and linear movement assemblies, or electrical cables between separated components. One of ordinary skill in the art would understand that such components can include transmitters, receivers (transceiving components), antennas, etc.

Figure 18A:
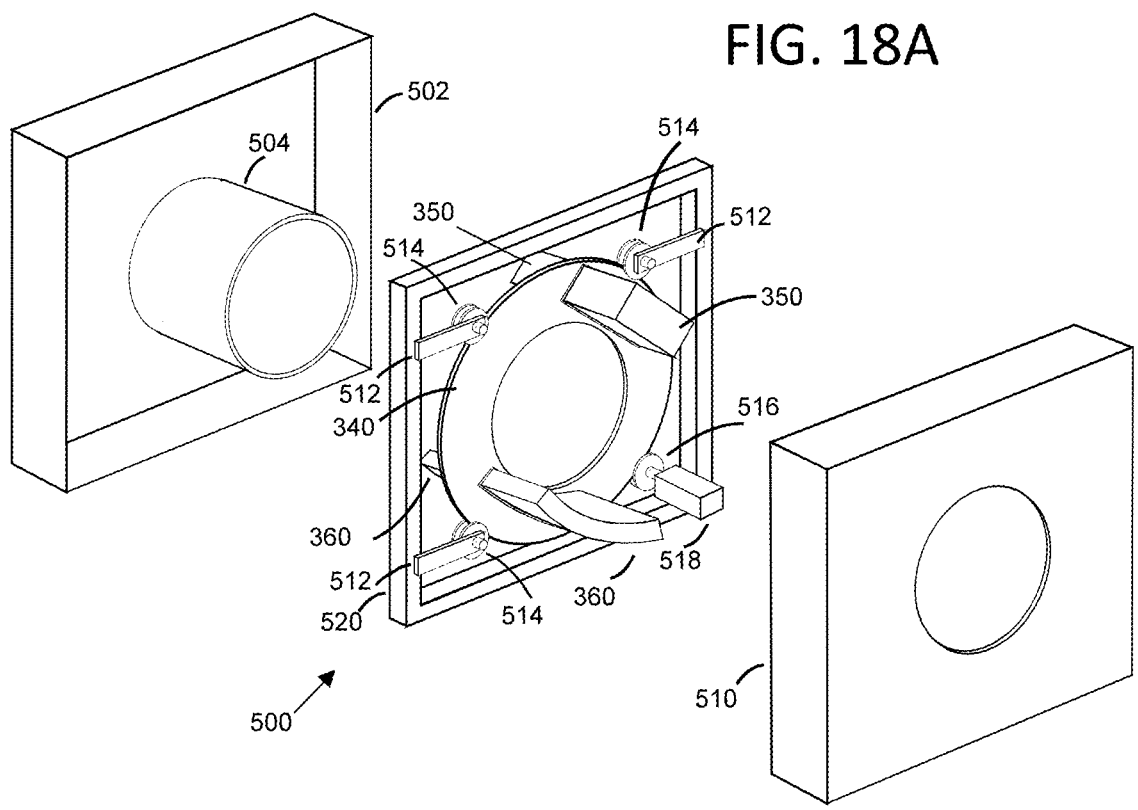
FIGS. 18A-18B illustrates a rotation mechanism for an X-ray detector and X-ray source, in accordance with one embodiment.
Figure 18B:
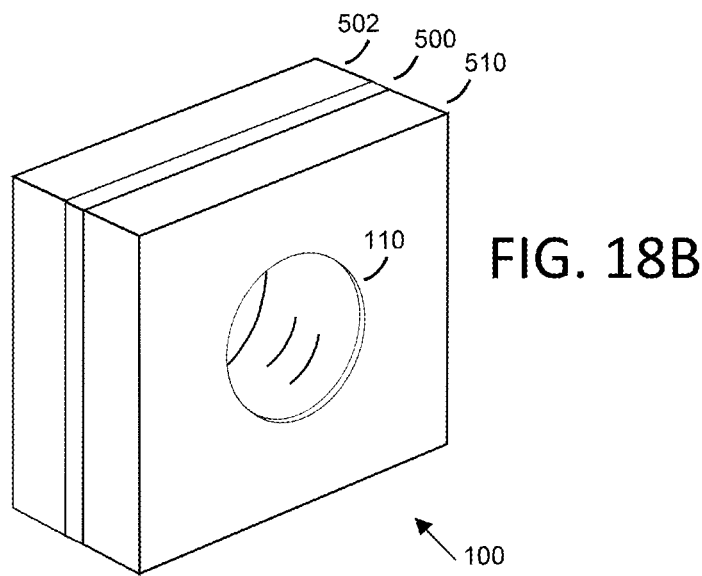

FIGS. 18A and 18B illustrate yet another contemplated embodiment. As described above with respect to FIG. 7, portable head CT scanner 100 may comprise a rotating plate 340 which supports X-ray source 350 and X-ray detector 360. Instead of a turntable bearing 304 being used, rotating plate 340 can be supported by rollers 514 and driven by a drive roller 516 and drive motor 518. Supporting the rotating plate 340 on rollers 514 enables components to be mounted on both sides of the rotating plate 340, allowing the entire rotating assembly to be precisely balanced with respect to all axes for more precise movement.

As shown in FIG. 18A, rollers 514 can be mounted on brackets 512 rigidly attached to a square outer frame 520. Brackets 512 may comprise any support structures to mount rollers 514. Frame 520 can replace the circular shaped enclosures present in previously described embodiments. However, frame 520 may vary in shape as desired. Drive roller 516 can be mounted on frame 520 against rotating plate 340, such that when drive roller 516 turns, rotating plate 340 turns accordingly. Drive roller 516 can be mounted to the shaft of drive motor 518, which can also be rigidly attached to frame 520. X-ray source 350 can be mounted to rotating plate 340 such that it passes through a matching rectangular opening in rotating plate 340. The center of X-ray source 350 can be positioned in the rectangular opening to center X-ray source 350 horizontally to be perpendicular to rotating plate 340. Similarly, X-ray detector 360 can be mounted to rotating plate 340 through a matching shaped opening in rotating plate 340. X-ray detector 360 can be similarly centered through rotating plate 340 to balance it alongside X-ray source 350.

Other components that may be disposed on the rotating plate 340, such as a battery, computer and control module, can be similarly mounted for precision balancing. The outer packaging in this embodiment may consist of a "clam shell" structure formed from a front cover 510 and a rear cover 502. Rear cover 502 may comprise a rear tube 504 providing the central bore as described above. Tube 504 can fit through rotating plate 340 and reach a similar bore located in the center of front cover 510. Tube 504 can connect the front and rear covers to form the central bore where the patient's head is inserted for scanning. This configuration may provide additional compact features and less moving parts. As illustrated in FIG. 18B, the portable head CT scanner 100 does not need to retract or extend and can maintain a single configuration. This portable head CT scanner 100 can pair with translational mechanisms such as that of rack 280 and pinion 432 (in FIG. 15) or linear actuator 386 (in FIG. 16) to translate the head CT scanner during the scanning process. It should be understood that the various translational and rotating mechanisms describe herein can be combined with the different examples and head CT scanner configurations. These mechanisms can be applied to various scanner-bed board assemblies as required.

Figure 19:
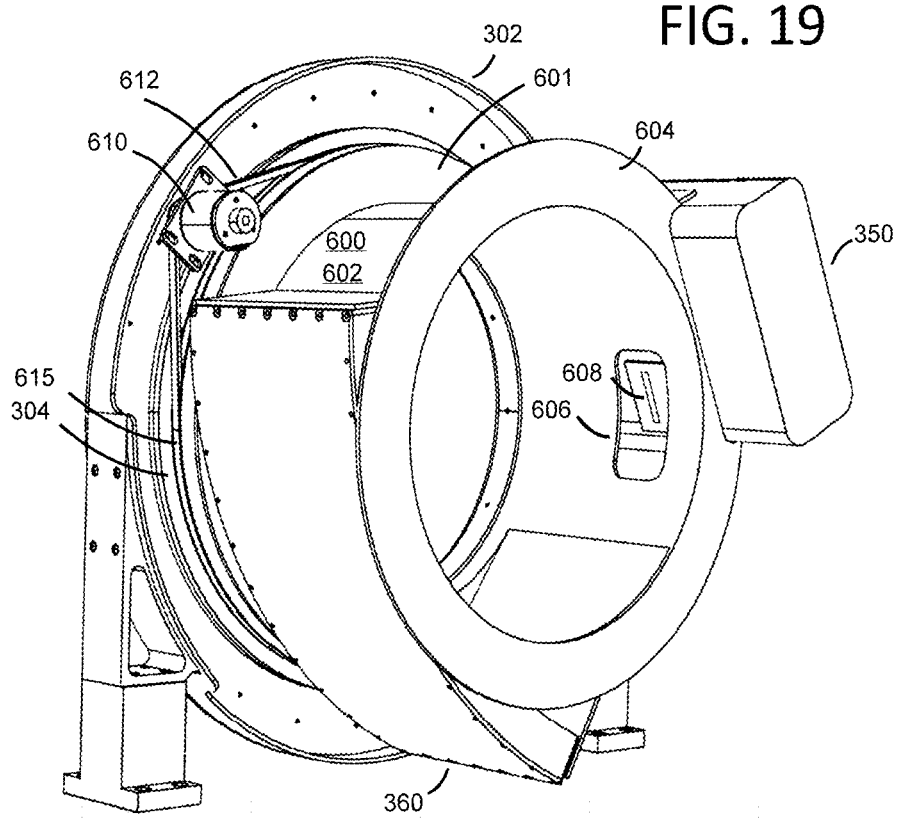
FIG. 19 illustrates an example CT scanner with a rotation mechanism, in accordance with one embodiment.
Figure 20:
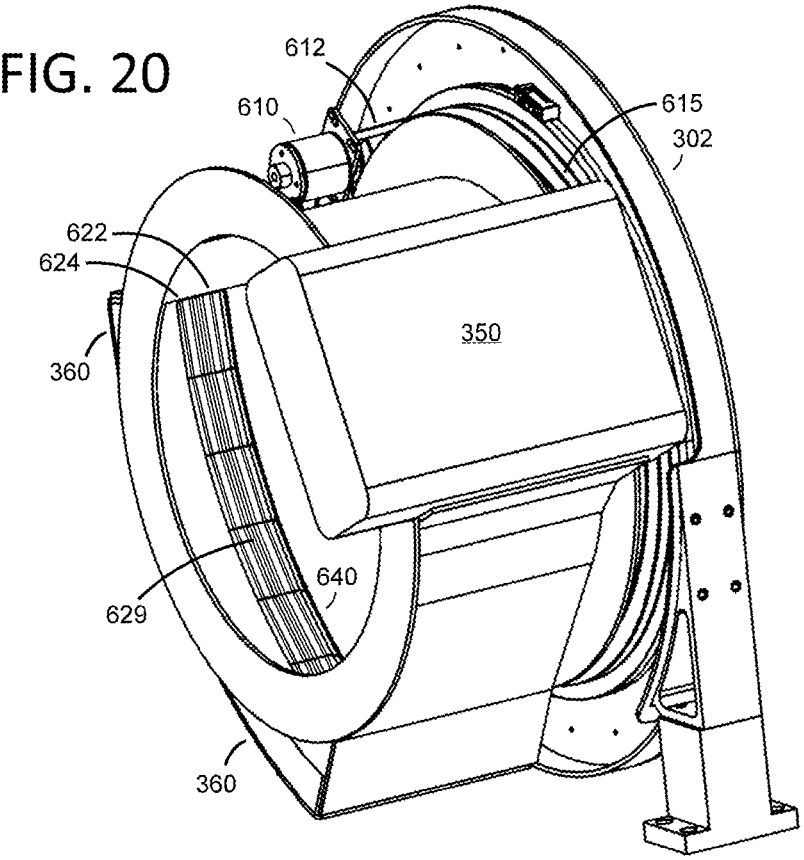
FIG. 20 illustrates a scatter X-ray detection system in accordance with some embodiments.

FIGS. 19 and 20 are different perspective views of an additional embodiment of an inner rotating assembly. As previously described in accordance with other embodiments, turntable bearing 304 can join rear plate 302 with a rotating plate 340. As shown in FIG. 19, rotating plate 601 is an embodiment of rotating plate 340. However, the X-ray source 350 and X-ray detector 360 need not mount directly to rotating plate 601. Rather, rotating plate 601, circular tube 602, and a front rotating plate 604 can be affixed to form a rotating drum 600. X-ray source 350, X-ray detector 360, and all other rotating components can be rigidly mounted to the rotating drum 600. As shown in the example of FIGS. 19 and 20, X-ray detector 360 can be centered on the circular tube 602 to surround a portion of rotating drum 600. X-ray source 350 can be oriented opposite X-ray detector 350 and similarly centered on circular tube 602. In this embodiment, the X-ray source 350 and X-ray detector 360 may have essentially the same positioning and orientation with respect to each other and to the axis of rotation, as previously described embodiments. However, mounting for these components is provided by a rotating drum 600 rather than directly to a rotating plate 340. In some embodiments, use of rotating drum 600 may provide greater rigidity and precision in alignment of the X-ray source with the X-ray detector.

X-rays can be generated by X-ray source 350 and pass through an X-ray collimating aperture 608 (similar to collimating aperture 350a in FIG. 7) that defines the thickness and angle of the X-ray fan beam, e.g., X-ray fan beam 364. X-ray fan beam 364 can pass through a source drum opening 606 (illustrated in FIG. 19) and a detector drum opening 640 (illustrated in FIG. 20) to strike X-ray detector 360. Rotating drum 600 can be rotated by a motor 610 mounted to rotating drum 600. A v-belt 612 can pass over a pulley on the shaft of motor 610 and around a circular grove 615 on rear plate 302. Circular grove 615 may run along the circumference of rear plate 302 such that v-belt 612 surrounds rear plate 302. In one example, the circular grove 615 may be approximately 19 inches in diameter and one-quarter inch wide and deep. Motor 610 can pull itself along v-belt 612 when activated, causing the rotating drum 600 to turn. Motor 610 may comprise a smooth or toothed pully as needed to mesh with v-belt 612. Since motor 610 is attached to rotating drum 600, rotating drum 600 can turn on turntable bearing 304 to rotate the entire imaging assembly. Alternatively, motor 610 may be mounted on the stationary rear plate 302 with v-belt 612 passing over a circular slot in the rotating drum 600, thereby causing it to rotate. The v-belt 612 may be properly tensioned with a spring load assembly or other methods.

Figure 21:
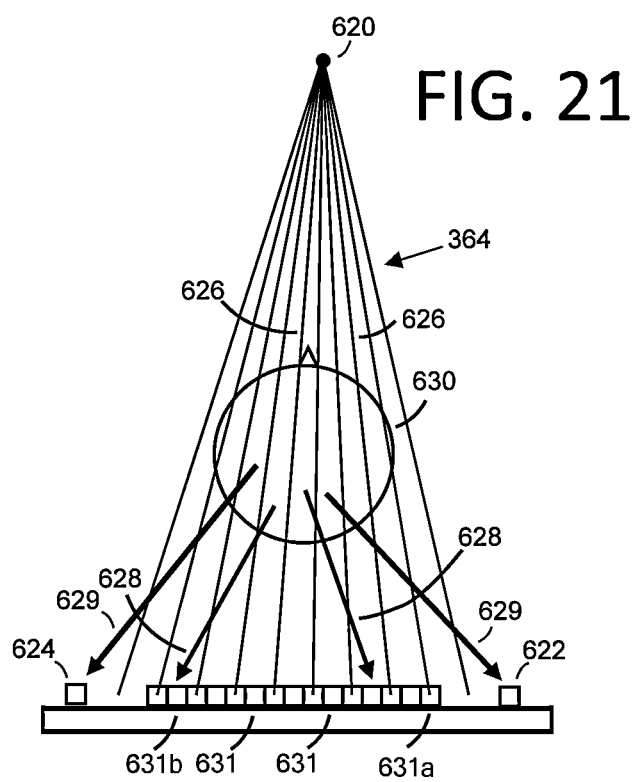
FIG. 21 illustrates the scatter X-ray detection system of FIG. 20 as X-rays reach the X-ray detector, in accordance with some embodiments.

X-ray CT imaging requires accurate measurements of the X-rays passing along straight lines from the X-ray source to the multitude of detector elements. One factor interfering with these measurements is scattered X-rays. As shown in FIG. 21, X-ray fan beam 364 can be emitted from the X-ray source focal spot 620 and move through the patient's head 630. Many of the X-rays comprising X-ray fan beam 364 pass in relatively straight lines to detector elements 631. Detector elements 631 are the multitude of physical areas of the X-ray detector 360 that are sensitive to X-rays. In one embodiment, illustrated in FIG. 20, the detector elements 631 form a two-dimensional array of 16 detector elements wide in the translational direction and 336 elements along the curved path in the rotational plane. Each detector element 631 has a sensitive area of one millimeter by one millimeter, making the entire sensitive area sixteen millimeters wide by 336 millimeters along the curve. Each detector element 631 tallies the number of X-rays that have struck its active area during a short period of time, such as 0.1 to 10 milliseconds, and transfers this information to the system computer in a digital form, where it typically becomes the value of an image pixel. In an ideal case, each X-ray passing through the patient head 630 will either continue on in a straight line 626 and be detected by detector elements 631, e.g., detector element 631a, or they may be absorbed in the tissue of the patient's head 630 and accordingly, may not be detected. However, some X-rays will scatter from the tissue in patient head 630 in random directions. Some of these scattered X-rays are directed away from the X-ray detector elements 631. These scattered X-rays have no impact on the resulting image.

On the other hand, some of the scattered X-rays 628 will point towards a detector element 631 and randomly strike one of the detector elements 631, such as detector element 631b. Traditional CT scanners typically position the X-ray detector about 18 inches from the patient. This orientation results in 1-2% of the X-rays received by the detector elements 631 being scattered X-rays. This low fraction of scattered X-rays only minimally reduces the resulting image quality. However, the fraction of scattered X-rays increases rapidly as the scanner is made smaller. In the case of the disclosed embodiments, the distance between the patient and the X-ray detector may only be a few inches, corresponding to the distance between the X-ray source and X-ray detector being about twice the diameter of the human head. In this configuration, approximately 15% of the detected X-rays are scattered rays. Without correction, these scattered X-rays could cause overwhelming degradation in a reconstructed CT scan image.

Embodiments of the present invention resolve this by additional x-ray detectors to measure the level of scattered x-rays. These measurements can be digitally subtracted from the detector signal to reduce the degradation of the reconstructed image. Scatter X-ray detectors (e.g. detectors 622 and 624) can be positioned near the main detector elements 631, but outside of the direct X-ray fan beam 364. Scatter detectors 622/624 may be placed in various orientations and distances from the main detector elements. In the example of FIG. 21, scatter detectors 622 and 624 can comprise two linear arrays each, one element wide and 336 elements long, positioned about four millimeters away from and running parallel to main detector elements 631. As shown in FIG. 21, scatter detectors 622 and 624 can be positioned outside of the main X-ray fan beam 364, because of their spacing from main detector elements 631. Main detector elements 631 will therefore receive transmitted X-rays 626 plus scattered X-rays 628. Scatter detector arrays 622 and 624 will receive only scattered X-rays 629 because the arrays are outside of the direct X-ray fan beam 364. The number of scattered X-rays 628 striking each detector element 631 is about the same as the number of scattered X-rays 629 striking each element of scatter detectors 622 and 624. Therefore, subtracting the number of X-rays measured by scatter detector elements 622,624 from the number of X-rays measured by the main detector elements 631, produces a good approximation of the number of X-rays passing in a straight line to the main detector elements 631. This scatter-corrected data is then used in the CT reconstruction process, thereby allowing the portable head CT scanner to produce good quality images despite the high scatter levels inherent in its ultra-compact size.

In some embodiments, measurements can be taken from scatter detectors 622 and 624 simultaneously with the data acquisition from detector elements 631. For each viewing angle, the main detector array 631 can produce 336×16 measurements and each of the two scatter detectors 622 and 624 can produce 336 measurements. In one embodiment, each of the 336×16 measurements from the detector array can be corrected for scatter by simply subtracting the measurement produced by the nearest scatter detector element. In another embodiment, each of the 336×16 detector elements 631 will be located on a straight line between a scatter detector element in one linear array 622, and a scatter detector element in the other linear array 624. Therefore, linear interpolation can be used to determine the appropriate level of scatter to subtract, using a combination of the two scatter measurements, and their relative distances from the detector element being corrected. This general procedure can further comprise interpolating between many elements in scatter detectors 622 and 624. This can create a best-fit two-dimensional map of the estimated scatter over the 336×16 detector element region based on the two 336 element scatter detectors.

Figure 22A:
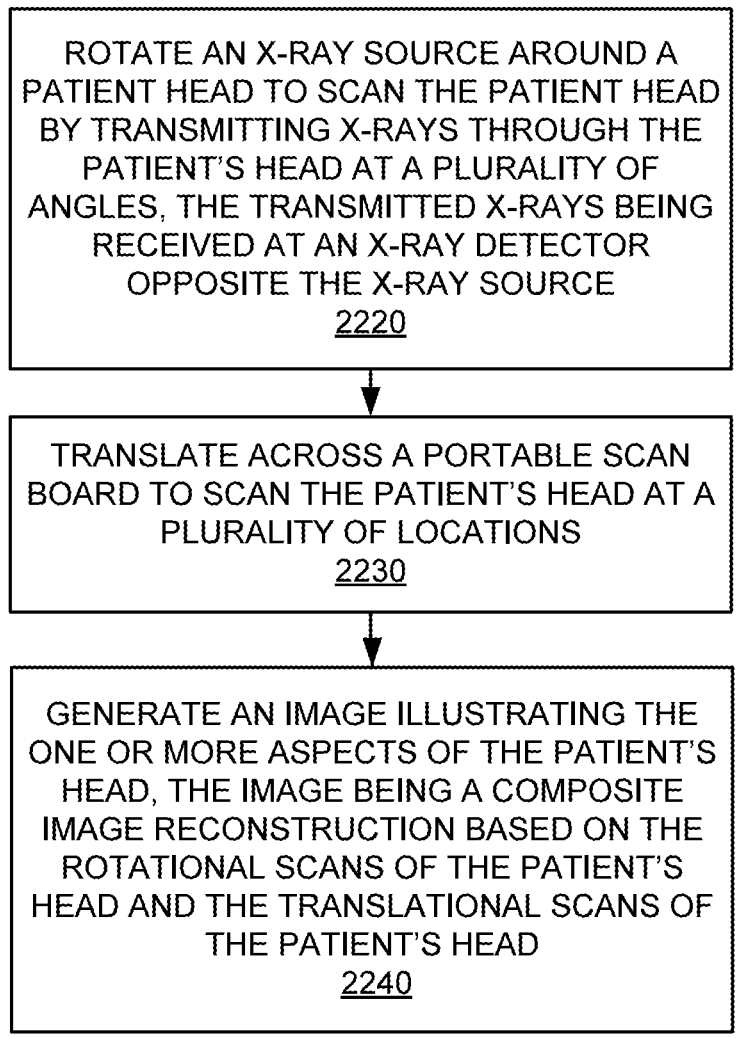
FIG. 22A illustrates a CT scanning operation in accordance with some embodiments.

FIG. 22A illustrates an example scanning operation that may be performed in accordance with embodiments of the disclosed technology. As discussed above, a portable CT scanning unit to scan a patient's head, e.g., portable head CT scanner 100, may be used in conjunction with a portable scan board, e.g., scan board 200. Accordingly, portable head CT scanner 100 and scan board 200 may, together, form a portable CT scanning unit or assembly. A patient may be positioned on the portable scan board, e.g., the torso of a patient may be lifted onto and laid to rest atop an incline portion of the portable scan board (torso support), elevating the head of the patient (which is resting on a head support) such that the portable CT scanner can rotate/translate about the patient's head.

At operation 2220, an X-ray source is rotated around the patient head to scan the patient head by transmitting X-rays through the patient's head at a plurality of angles, the transmitted X-ray beams being received at an X-ray detector opposite the X-ray source. As discussed above, various configurations/designs may be effectuated such that the portable CT scanner can rotate around the entirety of a patient's head while scanning the patient's head. The X-ray detector may be a curved detector comprising a plurality of detector cards, and the X-ray source may emit an X-ray fan beam. The number of X-rays detected by the X-ray detector is such that accuracy and precision of an image can at least match that of a traditional CT scanner, while the power needed for the X-ray scanning is much less than that needed for a traditional CT scanner.

At operation 2230, the portable CT scanner translates across the portable scan board to scan the patient's head at a plurality of locations. As discussed above, CT scanning in accordance with embodiments of the disclosed technology includes scanning during translation of the X-ray source/detector along the patient's head (via the scan board) so that different aspects/portions of the subject, e.g., patient's head, can be captured ("cross-sectional slices"). CT scanning in accordance with embodiments of the disclosed technology also includes scanning during rotation the X-ray source/detector (e.g., per operation 2220) so that the patient's head can be scanned/imaged at different angles relative to the circumference of the patient's head.

At operation 2240, an image is generated illustrating one or more aspects of the patient's head, wherein the image is a composite image reconstruction based on the rotational scans of the patient's head and the translational scans of the patient's head. A foundational principle of computed tomography is that images of the interior of an object can be created in a computer from sufficient X-ray measurements of the object taken at a multitude of angles. As delineated at operation 2240, sufficiency of the multitude of angles is described by "rotational scans of the patient's head and the translation of the patient's head." As further delineated at operation 2240, the term "reconstruction" is known in the art of CT scanning to mean the computerized process of converting the angular X-ray measurements into an image of the object's interior.

Figure 22B:
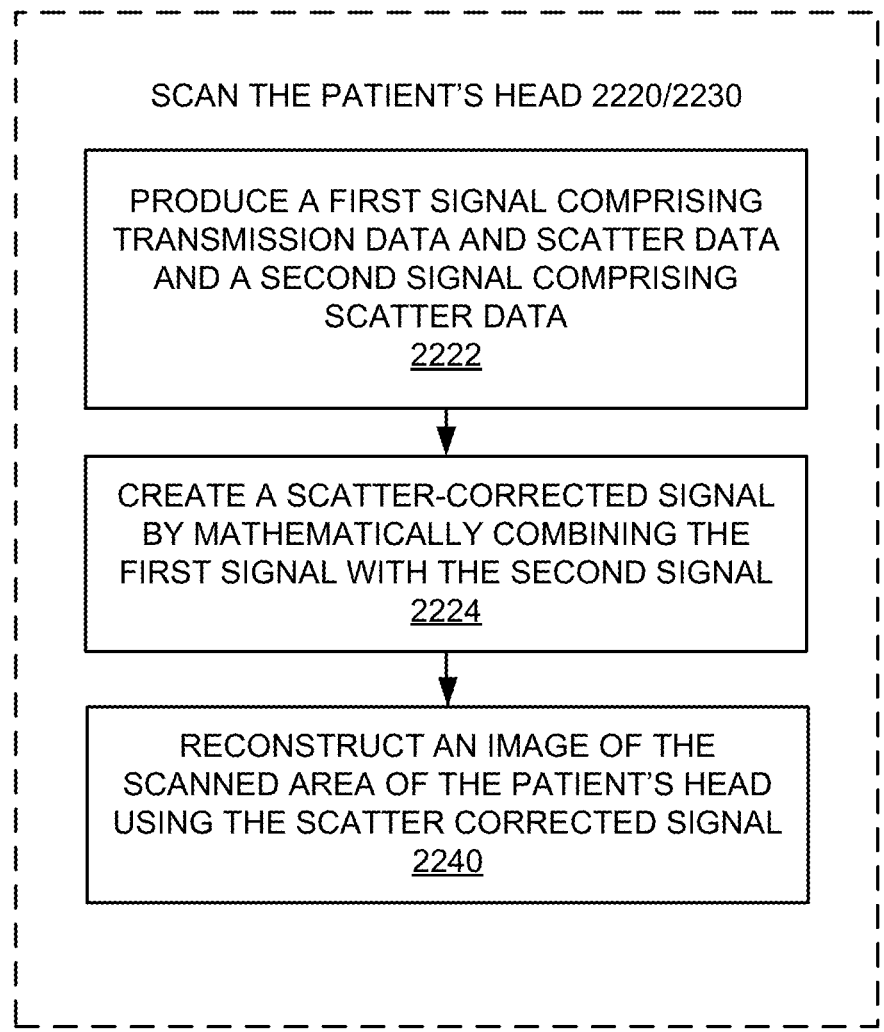
FIG. 22B illustrates an example scanning method using a scatter-corrected signal for effectuating the CT scanning operation of FIG. 22A.

FIG. 22B illustrates an example method for correcting scatter X-rays in accordance with the systems described above.

At operation 2222, a first signal comprising transmission data and scatter data and a second signal comprising scatter data may be produced. As described above, scatter detectors may be placed in various orientations and distances from main detector elements. As an example, scatter detectors may be placed adjacent to the main detector elements. Main detector elements can receive transmitted X-rays plus scattered X-rays. Scatter detectors can receive only scattered X-rays because they are outside the reach of the X-ray fan beam transmitted by the X-ray source.

At operation 2224, a scatter-corrected signal may be created by mathematically combining the first signal with the second signal. In some embodiments, this correction can comprise subtracting the measurement values produced by the nearest scatter detector element from those of the corresponding main detector element. In other embodiments, the approximate amount of scatter added to each detector element can be found by linear interpolation using the measured scatter level. This general procedure can further comprise interpolating between many elements in the scatter detectors.

At operation 2240, an image of the patient's head may be reconstructed using the scatter-corrected signal. As previously described, "reconstruction" is known in the art of CT scanning, meaning that the angular measurements (i.e., the scatter-corrected signal) are converted into one or more images of the interior of the object being examined (the patient's head) through the use of a computerized algorithm.

Embodiments of the disclosed technology enable CT scanning of a subject, e.g., a patient's head, while they remain in their bed or current position, with only minimal movement of their body. In part, this is accomplished by overcoming at least the following problems associated with traditional/transportable CT scanners: the inability to reconstruct images from an unconventional X-ray geometry (resulting from small form factor constraints); the instability of a surface on which a subject is positioned, e.g., a bed's mattress; lower X-ray power resulting from a small form factor CT scanner, e.g., portable head CT scanner 100; and an excessive level of scattered X-rays. Such problems can be addressed/overcome by embodiments of the disclosed technology that contemplate a small and unique mechanical design, a shorter SID, a wider X-ray detector, scatter detection and correction using dedicated detectors, iterative reconstruction using GPUs, and a scan board for stabilizing the patient relative to a portable head CT scanner working in conjunction with the scan board. Embodiments of the disclosed technology further contemplate a telescoping package or assembly that facilitates storage and transport, and that allows for single-person transport of the portable head CT scanner in a carrying case.

Those skilled in the design of X-ray imaging systems will recognize that many variations exist within the scope of the embodiments described herein, including: variations in the packaging shape, size, and materials; variations in materials, such as metal, plastic, fiberglass and carbon fiber; various methods of connecting the scanner to the bed board; different friction reducing methods in the alignment bars and grooves; alternative handle designs for lifting and positioning the scanner; equivalent motors and actuators for scanning the beam over the patients head; other methods of moving and controlling the rotating plate and its components; changes to the X-ray fan beam; and alternative digital computers and communication links.

Figure 23:
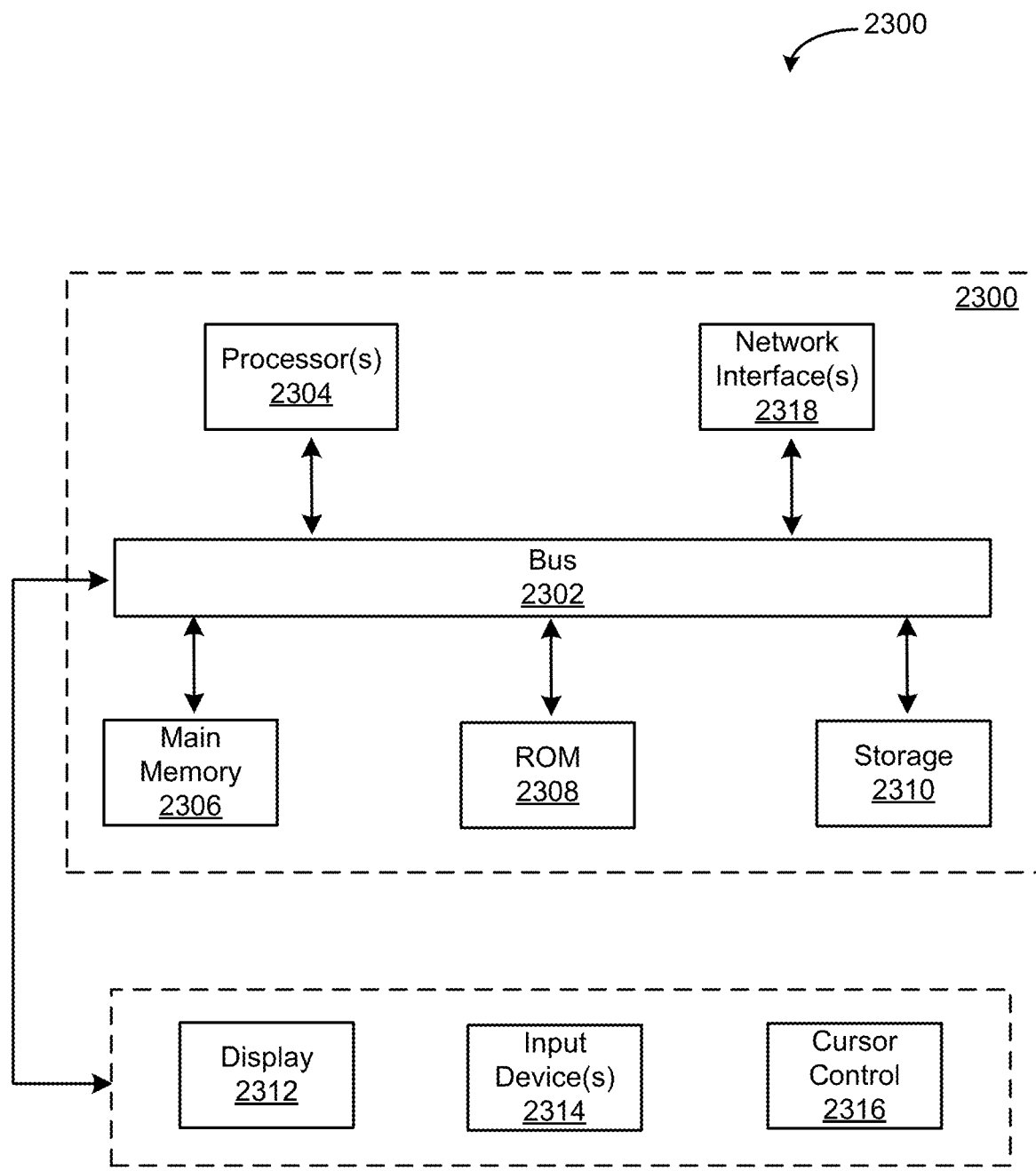
FIG. 23 illustrates an example computing component in accordance with various embodiments described herein.

FIG. 23 depicts a block diagram of an example computer system 2300 which can be applied to various embodiments described herein. The computer system 2300 includes a bus 2302 or other communication mechanism for communicating information, one or more hardware processors 2304 coupled with bus 2302 for processing information. Hardware processor(s) 2304 may be, for example, one or more general purpose microprocessors.

The computer system 2300 also includes a main memory 2306, such as a random access memory (RAM), cache and/or other dynamic storage devices, coupled to bus 2302 for storing information and instructions to be executed by processor 2304. Main memory 2306 also may be used for storing temporary variables or other intermediate information during execution of instructions to be executed by processor 2304. Such instructions, when stored in storage media accessible to processor 2304, render computer system 2300 into a special-purpose machine that is customized to perform the operations specified in the instructions.

The computer system 2300 further includes a read only memory (ROM) 2308 or other static storage device coupled to bus 2302 for storing static information and instructions for processor 2304. A storage device 2310, such as a magnetic disk, optical disk, or USB thumb drive (Flash drive), etc., is provided and coupled to bus 2302 for storing information and instructions.

The computer system 2300 may be coupled via bus 2302 to a display 2312, such as a liquid crystal display (LCD) (or touch screen), for displaying information to a computer user. An input device 2314, including alphanumeric and other keys, is coupled to bus 2302 for communicating information and command selections to processor 2304. Another type of user input device is cursor control 2316, such as a mouse, a trackball, or cursor direction keys for communicating direction information and command selections to processor 2304 and for controlling cursor movement on display 2312. In some embodiments, the same direction information and command selections as cursor control may be implemented via receiving touches on a touch screen without a cursor.

The computing system 2300 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 2300 may implement the techniques described herein using customized hard-wired logic, one or more ASICs or FPGAs, firmware and/or program logic which in combination with the computer system causes or programs computer system 2300 to be a special-purpose machine. According to one embodiment, the techniques herein are performed by computer system 2300 in response to processor(s) 2304 executing one or more sequences of one or more instructions contained in main memory 2306. Such instructions may be read into main memory 2306 from another storage medium, such as storage device 2310. Execution of the sequences of instructions contained in main memory 2306 causes processor(s) 2304 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 2310. Volatile media includes dynamic memory, such as main memory 2306. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 2302. Transmission media can also take the form of acoustic or light waves, such as those generated during radio-wave and infra-red data communications.

The computer system 2300 also includes a communication interface 2318 coupled to bus 2302. Network interface 2318 provides a two-way data communication coupling to one or more network links that are connected to one or more local networks. For example, communication interface 2318 may be an integrated services digital network (ISDN) card, cable modem, satellite modem, or a modem to provide a data communication connection to a corresponding type of telephone line. As another example, network interface 2318 may be a local area network (LAN) card to provide a data communication connection to a compatible LAN (or WAN component to communicated with a WAN). Wireless links may also be implemented. In any such implementation, network interface 2318 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 2318, which carry the digital data to and from computer system 2300, are example forms of transmission media.

The computer system 2300 can send messages and receive data, including program code, through the network (s), network link and communication interface 2318. In the Internet example, a server might transmit a requested code for an application program through the Internet, the ISP, the local network and the communication interface 2318.

The received code may be executed by processor 2304 as it is received, and/or stored in storage device 2310, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 2300.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A portable computerized tomography (CT) scanning assembly to scan a patient's head, comprising:
    a portable scan board on which a patient is positioned; and
    a portable CT scanner positioned onto the portable scan board, the portable CT scanner and the portable scan board forming the portable CT scanning assembly, the portable CT scanner being operative to:
        rotate an X-ray source around the patient's head to scan the patient's head by transmitting X-rays through the patient's head at a plurality of angles, the transmitted X-rays being received by an X-ray detector opposite the X-ray source;
        translate across the portable scan board to scan the patient's head at a plurality of locations; and
        generate an image illustrating one or more aspects of the patient's head, the image being a composite image reconstruction based on the rotational and translational scanning of the patient's head.

2. The portable CT scanning assembly of claim 1, wherein the portable CT scanner and the portable scan board lockingly engage such that portable scan board prevents relative movement between the portable CT scanner and the patient.

3. The portable CT scanning assembly of claim 2, wherein portable CT scanner and the portable scan board comprise corresponding alignment elements to effectuate the locking engagement between the portable CT scanner and the portable scan board.

4. The portable CT scanning assembly of claim 3, wherein the corresponding alignment elements comprises one or more alignment elements of the portable CT scanner and one or more alignment elements of the portable scan board.

5. The portable CT scanning assembly of claim 4, wherein the portable scan board defines a first position for the portable CT scanner and a second position for the portable CT scanner, the first position locating the portable CT scanner such that the patient's head is outside a scan area of the portable CT scanner, the second position locating the portable CT scanner such that an entirety of the patient's head is within the scan area of the portable CT scanner.

6. The portable CT scanning assembly of claim 5, wherein the one or more alignment elements of the portable CT scanner slidingly mate with the one or more alignment elements of the portable scan board facilitating movement of the portable CT scanner between the first and the second positions.

7. The portable CT scanning unit of claim 1, wherein the portable scan board comprises an incline plane relative to a base surface of the portable scan board.

8. The portable CT scanning unit of claim 7, wherein the incline plane acts as a torso support elevating the patient's torso from a surface on which the patient is lying and atop which, the portable scan board rests, the incline plane being positioned underneath the patient.

9. The portable CT scanning unit of claim 8, wherein the surface atop which the portable scan board rests comprises a surface of a bed.

10. The portable CT scanning assembly of claim 1, wherein at least the portable CT scanner has physical dimensions facilitating storage of the portable CT scanner within a hand-movable case for transport.

11. The portable CT scanning assembly of claim 1, wherein a distance between the X-ray source and the X-ray detector is approximately two times greater than a diameter of the patient's head.

12. A portable computerized tomography (CT) scanning assembly to scan a patient's head, comprising:
a portable scan board on which a patient is positioned; and
a portable CT scanner positioned and locked onto the portable scan board, the portable CT scanner and the portable scan board forming the portable CT scanning assembly, the portable CT scanner being operative to:
perform a CT scan operation of the patient's head by:
rotating an X-ray source around the patient's head at a plurality of angles while transmitting an X-ray fan beam through the patient's head towards an X-ray detector correspondingly rotating about the patient's head; and
extending and retracting front and rear components of the portable CT scanner translating the X-ray source and X-ray detector across one or more portions of the patient's head along a longitudinal axis of the patient's head; and
generate a composite image representing the one or more portions of the patient's head at the plurality of angles.

13. The portable CT scanning assembly of claim 12, wherein the portable CT scanner and the portable scan board lockingly engage such that portable scan board prevents relative movement between the portable CT scanner and the patient.

14. The portable CT scanning assembly of claim 2, wherein portable CT scanner and the portable scan board comprise corresponding alignment elements to effectuate the locking engagement between the portable CT scanner and the portable scan board.

15. The portable CT scanning assembly of claim 14, wherein the portable scan board defines a first position for the portable CT scanner and a second position for the portable CT scanner, the first position locating the portable CT scanner such that the patient's head is outside a scan area of the portable CT scanner, the second position locating the portable CT scanner such that an entirety of the patient's head is within the scan area of the portable CT scanner.

16. The portable CT scanning assembly of claim 15, wherein the one or more alignment elements of the portable CT scanner slidingly mate with the one or more alignment elements of the portable scan board facilitating movement of the portable CT scanner between the first and the second positions.

17. The portable CT scanning unit of claim 12, wherein the portable scan board comprises an incline plane relative to a base surface of the portable scan board, the incline plane acting as a torso support elevating the patient's torso from a surface on which the patient is lying and atop which, the portable scan board rests, the incline plane being positioned underneath the patient.

18. The portable CT scanning unit of claim 17, wherein the surface atop which the portable scan board rests comprises a surface of a bed.

19. The portable CT scanning assembly of claim 12, wherein at least the portable CT scanner has physical dimensions facilitating storage of the portable CT scanner within a hand-movable case for transport.

20. The portable CT scanning assembly of claim 12, wherein a distance between the X-ray source and the X-ray detector is approximately two times greater than a diameter of the patient's head.

* * * * *